United States Patent [19]

Gymer et al.

[11] Patent Number: 5,023,258
[45] Date of Patent: Jun. 11, 1991

[54] TRIAZOLE ANTIFUNGAL AGENTS

[75] Inventors: Geoffrey E. Gymer, Sandwich; Subramaniyan Narayanaswami, Deal; Kenneth Richardson, Birchington, all of England

[73] Assignee: Pfizer Inc., New York, N.Y.

[21] Appl. No.: 368,692

[22] Filed: Jun. 20, 1989

[51] Int. Cl.$^5$ .............. A61K 31/495; C07D 417/12; C07D 403/12; C07D 403/14
[52] U.S. Cl. .................... 514/255; 514/252; 544/60; 544/121; 544/357; 544/360; 544/366; 544/370; 544/372; 71/92
[58] Field of Search ............... 71/92; 544/60, 121, 544/358, 357, 360, 366, 370, 372; 514/255, 252

[56] References Cited

U.S. PATENT DOCUMENTS 4,402,957 9/1983 Heeres et al. .................. 514/254
4,623,654 11/1986 Parry et al. .................... 548/262
4,868,196 9/1989 Holmwood et al. ............ 548/262

FOREIGN PATENT DOCUMENTS 0118138 9/1984 European Pat. Off. .
152596 8/1985 European Pat. Off. .
0237963 9/1987 European Pat. Off. .

Primary Examiner—Jane T. Fan
Assistant Examiner—Celia Chang
Attorney, Agent, or Firm—Peter C. Richardson; J. Trevor Lumb; James M. McManus

[57] ABSTRACT

The invention provides triazole antifungal compounds of the formula:

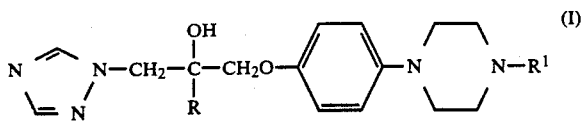

wherein R is either
(a) a phenyl group optionally substituted with 1 to 3 substituents, each selected independently from halo and CF$_3$; or
(b) a 5-chloropyridin-2-yl group; and R$^1$ is either
(a) a phenyl group, para-substituted by a group selected from the following:

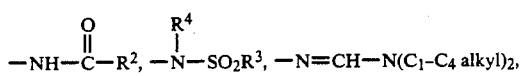

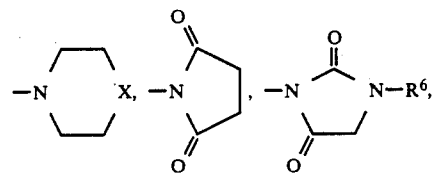

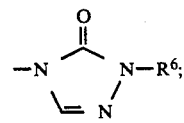

or (b) a 2-, 3- or 4-pyridinyl group optionally substituted with a group of the formula 10 Claims, No Drawings

5,023,258

TRIAZOLE ANTIFUNGAL AGENTS

BACKGROUND OF THE INVENTION

This invention relates to novel triazole derivatives which have antifungal activity and are useful in the treatment of fungal infections in animals, including humans, and as agricultural fungicides.

SUMMARY OF THE INVENTION

According to the invention, there are provided compounds of the formula:

(I)

[Structure: triazole-$CH_2$-C(OH)(R)-$CH_2O$-phenyl-N(piperazine)N-$R^1$]

and their pharmaceutically and agriculturally acceptable salts, wherein
R is either (a) a phenyl group optionally substituted with 1 to 3 substituents, each selected independently from halo and $CF_3$; or (b) a 5-chloropyridin-2-yl group:
$R^1$ is either
(a) a phenyl group, para-substituted by a group selected from the following:

(i) $-NH-\overset{\overset{O}{\|}}{C}-R^2$ where $R^2$ is selected from $C_1-C_4$ alkyl, $C_3-C_7$ cycloalkyl, 2-chloropyridin-3-yl, $C_1-C_4$ alkoxy, allyloxy and ($C_1-C_4$ alkyl)amino (ii) $-\overset{\overset{R^4}{|}}{N}-SO_2R^3$ where either $R^3$ is selected from $C_1-C_4$ alkyl, halo-($C_1-C_4$ alkyl) and di-($C_1-C_4$ alkyl)amino and $R^4$ is H or methyl; or $R^3$ and $R^4$ taken together constitute a $C_3$ or $C_4$ alkylene group
(iii) $-N=CH-N(C_1-C_4\ alkyl)_2$ (iv) [piperazine-type ring with X]

where X is O, $SO_2$ or N-$R^5$, where $R^5$ is H, $C_1-C_4$ alkyl or $C_1-C_4$ alkanoyl
and (v) [succinimide], [hydantoin-like N-$R^6$], or [triazolinone N-$R^6$]

where $R^6$ is $C_1-C_4$ alkyl;
or (b) a 2-, 3- or 4-pyridinyl group optionally substituted with a group of the formula

[Structure: -N(C=O)N-$R^6$ with N=N]

where $R^6$ is $C_1-C_4$ alkyl.

$C_3$ and $C_4$ alkyl and alkoxy groups and $C_4$ alkanoyl groups may be straight or branched chain. "Halo" means F, Cl, Br or I. The preferred haloalkyl groups are 3-chloroprop-1-yl and 2,2,2-trifluoroethyl.

When R is a substituted phenyl group this includes, for example, 4-fluorophenyl, 4-chlorophenyl, 4-bromophenyl, 4-iodophenyl, 4-trifluoromethylphenyl, 2-fluorophenyl, 2-chlorophenyl, 2,4-dichlorophenyl, 2,4-difluorophenyl, 2-chloro-4-fluorophenyl, 2-fluoro-4-chlorophenyl, 2,5-difluorophenyl, 2,4,6-trifluorophenyl and 4-bromo-2,5-difluorophenyl.

The preferred compounds are those wherein R is dichlorophenyl or difluorophenyl and $R^1$ is para-substituted phenyl by one of the following groups:

(i) $-NH-\overset{\overset{O}{\|}}{C}-R^2$ where
$R^2$ is methyl, 2-chloropyridin-3-yl, methoxy, ethoxy, allyloxy or but-1-ylamino (ii) $-\overset{\overset{R^4}{|}}{N}-SO_2R^3$ where
$R^4$ is H and $R^3$ is methyl, ethyl, prop-2-yl, 3-chloroprop-1-yl, 2,2,2-trifluoroethyl or N,N-dimethylamino; or $R^4$ is methyl and $R^3$ is methyl; or $R^3$ and $R^4$ are taken together and constitute a propylene group
(iii) $-N=CH-N(CH_3)_2$ (iv) [piperazine ring with X]

where
X is $SO_2$ or $NR^5$, where $R^5$ is H or acetyl;

(v) [succinimide], [hydantoin N-$CH_3$] or

[triazolinone N-$CH(CH_3)CH_2CH_3$] or (b) [pyridine-N],

[pyridyl-triazolinone N-$CH(CH_3)CH_2CH_3$] or

-continued

[Structure: pyridyl-N-piperazinone with N—CH(CH₃)CH₂CH₃ substituent]

Especially preferred are the compounds where R is 2,4-dichloro or 2,4-difluorophenyl and R¹ is

[Structure: phenyl-N(thiomorpholine-S,S-dioxide)]

or

[Structure: phenyl-N(piperazine-2,5-dione)—N—CH₃]

Within this invention there are also provided novel compounds of the formula (II), useful as synthetic intermediates for the preparation of compounds of the formula (I):

[Structure (II): triazolyl-CH₂-C(OH)(R)-CH₂O-phenyl-N(piperazine)N-phenyl-R⁸]

where
R⁸ represents —NO₂, —NH₂ or

—NHCOO—[phenyl], and R is as defined for formula (I).

The invention further provides a pharmaceutical composition comprising a compound of the formula (I) or a pharmaceutically acceptable salt thereof, together with a pharmaceutically acceptable diluent or carrier.

The invention further provides an antifungal composition for agricultural (including horticultural) use, comprising a compound of the formula (I) or an agriculturally acceptable salt thereof, together with an agriculturally acceptable diluent or carrier.

The invention yet further provides a method of treating an animal (including a human being), plant or seed to cure or prevent a fungal infection, which comprises treating said animal, plant or seed, or the locus of said plant or seed, with an effective amount of a compound of the formula (I) or with, as appropriate, a pharmaceutically or agriculturally acceptable salt thereof.

DETAILED DESCRIPTION OF THE INVENTION

The compounds of the formula (I) in which R¹ is a phenyl group, para-substituted by one of the following groups:

$$-NH-\overset{O}{\underset{\parallel}{C}}-R^2, \quad -NH-SO_2R^3, \quad -N=CH-N(C_1-C_4\,alkyl)_2,$$

[Structure: —N(succinimide)] or [Structure: —N(piperazine)X]

(where X is O, SO₂, NH or N—(C₁-C₄ alkyl), and R² and R³ are as defined for formula (I), can be prepared directly from the following intermediates:

[Structure (III): triazolyl-CH₂-C(OH)(R)-CH₂O-phenyl-N(piperazine)N-phenyl-NH₂]

where R is as defined for formula (I).
To prepare compounds in which R¹ is $$-[phenyl]-NH-\overset{O}{\underset{\parallel}{C}}-R^2,$$

where R² is C₁-C₄ alkyl, C₃-C₇ cycloalkyl or 2-chloropyridin-3-yl, compound (III) may be acylated with a carboxylic acid of the formula R²COOH in the presence of a suitable dehydrating agent, e.g. 1,1'-carbonyldiimidazole. Preferably R²COOH is used in the form of its "functional equivalent as an acylating agent", e.g. as a compound of the formula R²COCl, R²COBr or (R²CO)₂O, or with 2-chloronicotinic acid, more preferably in the form of an activated ester. Such activated esters are formed in situ between 2-chloronicotinic acid and, e.g., N-hydroxysuccinimide or 1-hydroxybenzotriazole, in the presence of a suitable dehydrating agent, e.g. 1,3-dicyclohexylcarbodiimide. The acylation is typically carried out at from 0° C. to the reflux temperature, preferably at from 0° C. to room temperature, in a suitable organic solvent, e.g. methylene chloride or tetrahydrofuran, and, when using an acid halide or an acid anhydride, preferably in the presence of an acid acceptor, e.g., triethylamine or pyridine.

To prepare compounds in which R¹ is

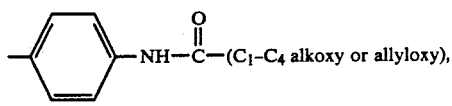

compound (III) is reacted with a chloroformate reagent of the formula ClCO($C_1$-$C_4$ alkoxy or allyloxy) in the presence of an acid acceptor such as triethylamine. The reaction is typically carried out at from 0° C. to room temperature, preferably at 0° C., in a suitable organic solvent, e.g. methylene chloride.

To prepare compounds where $R^1$ is

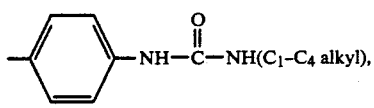

compound (III) is reacted with a $C_1$-$C_4$ alkyl isocyanate. The reaction is typically carried out at up to, and preferably at the reflux temperature in a suitable organic solvent, e.g. tetrahydrofuran.

To prepare compounds in which $R^1$ is

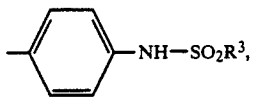

where $R^3$ is as defined for formula (I), compound (III) is reacted with a sulphonyl halide of the formula ($C_1$-$C_4$ alkyl or halo-[$C_1$-$C_4$ alkyl]).$SO_2$.(Cl or Br), a sulphonic anhydride of the formula ([$C_1$-$C_4$ alkyl or halo-($C_1$-$C_4$ alkyl)]$SO_2$)$_2$O or with a sulphamoyl chloride of the formula ($C_1$-$C_4$ alkyl)$_2$NSO$_2$Cl in the presence of a suitable acid acceptor, e.g., triethylamine or pyridine. The reaction is typically carried out at from 0° C. to the reflux temperature, preferably at from 0° C. to room temperature when a sulphonyl halide or sulphonic anhydride is used, and preferably at from room temperature to the reflux temperature when a sulphamoyl chloride is used, in a suitable organic solvent, e.g. methylene chloride.

To prepare compounds in which $R^1$ is

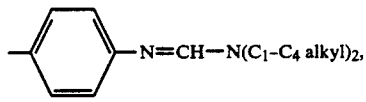

compound (III) is reacted with a dimethyl or diethyl acetal of the formula ($C_1$-$C_4$ alkyl)$_2$NCH($C_1$-$C_2$alkoxy)$_2$. The reaction is carried out in a suitable organic solvent, e.g. ethanol, at up to, and preferably at the reflux temperature.

To prepare compounds in which $R^1$ is

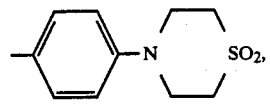

compound (III) is reacted with divinyl sulphone. The reaction is carried out in a suitable organic solvent, e.g. ethanol, at up to, and preferably at the reflux temperature of the solvent.

To prepare compounds in which $R^1$ is

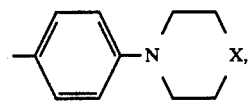

where
X is O, NH or N—($C_1$-$C_4$ alkyl) the following general scheme is used:

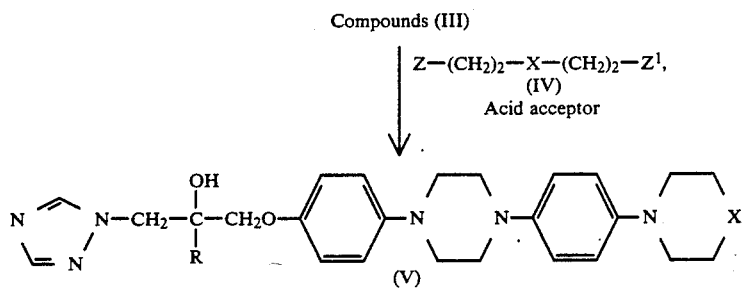

Z and $Z^1$ are leaving groups, e.g. Cl, Br or methanesulphonyloxy. Z and $Z^1$ are preferably Cl. Where X is NH or N-($C_1$-$C_4$ alkyl), the reagents of formula (IV) are conveniently used in acid addition salt form, e.g. as the hydrochloride. The reaction is typically carried out at up to, and preferably at the reflux temperature in a suitable organic solvent, e.g. ethanol, and in the presence of an acid acceptor such as potassium carbonate.

To prepare compounds (V) in which X is N—($C_2$-$C_4$ alkanoyl), compound (V) where X is NH, is acylated with a $C_2$-$C_4$ alkanoyl chloride or bromide, or with an acid anhydride of the formula ($C_2$-$C_4$ alkanoyl)$_2$O. The reaction is typically carried out at from 0° C. to room temperature in a suitable organic solvent, e.g. methylene chloride, and in the presence of a suitable acid acceptor, e.g. pyridine.

To prepare compounds (V) in which X is N—CHO, compound (V), where X is NH, is typically formylated with acetic-formic anhydride by conventional methods.

To prepare compounds in which $R^1$ is

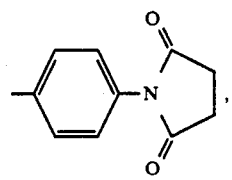

compound (III) is reacted with succinic anhydride. The reaction is typically carried out at up to, and preferably at the reflux temperature in a suitable acidic solvent medium, e.g. acetic acid.

To prepare compounds in which $R^1$ is

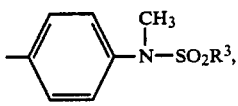

where
$R^3$ is as defined for formula (I), compound (I), where $R^1$ is

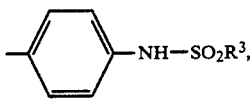

is reacted with a suitable methylating reagent, e.g. dimethyl sulphate, in the presence of a base, e.g. sodium hydroxide. The reaction is typically carried out at room temperature in a suitable solvent, e.g. aqueous THF.

To prepare compounds in which $R^1$ is

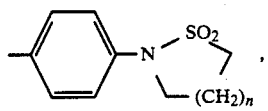

where
n is 1 or 2, compound (I), where $R^1$ is

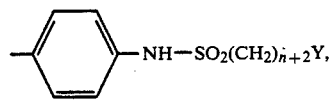

where
Y is halo, preferably Cl, is subjected to intramolecular cyclisation in the presence of a suitable base, e.g. sodium ethoxide. The reaction is typically carried out at, or just below, the reflux temperature in a suitable organic solvent, e.g. ethanol.

To prepare compounds in which $R^1$ is

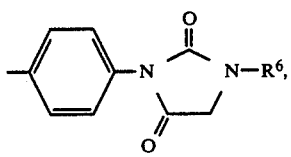

where
$R^6$ is as defined for formula (I), a compound (I), where $R^1$ is

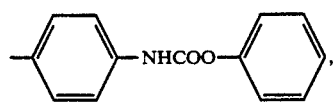

is reacted with a compound of the formula $R^6NHCH_2COO(C_1-C_2$ alkyl), which may be used in acid addition salt form, e.g. as the hydrochloride salt, provided a neutralising amount of a base such as sodium bicarbonate is present. The reaction is typically carried out at up to, and preferably at the reflux temperature in a suitable organic solvent, e.g. 1,4-dioxane, in the presence of a catalytic amount of 4-(N,N-dimethylamino)-pyridine.

The compounds where $R^1$ is

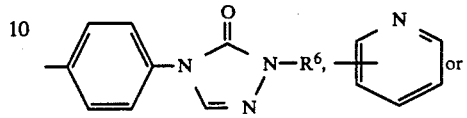

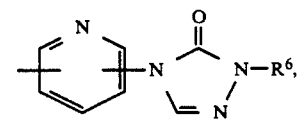

where
$R^6$ is as defined for formula (I), are prepared by the following general scheme:

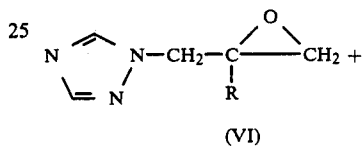

(VI)

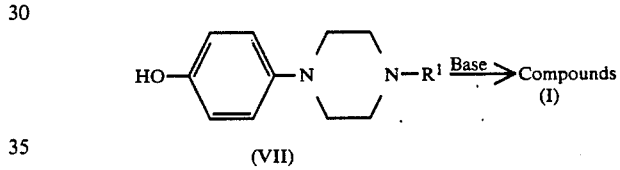

(VII)

The reaction is typically carried out at from 50° C. to the reflux temperature, preferably at between 60°–100° C., in a suitable organic solvent, e.g. dimethylformamide, in the presence of a suitable base, e.g. sodium hydride or cesium carbonate. The starting materials of the formula (VI) are known compounds (see e.g. EP-A-44605, EP-A-69442 and EP-A-0106515). The starting materials of formula (VII) are either known compounds (see J. Med. Chem., 27, 894 [1984], or are preparable by analogous methods thereto) or can be prepared conventionally, e.g. as described in the following Preparations section.

The starting materials of the formulae (II) and (III) can be prepared by the conventional techniques described in the following Preparations section.

All compounds can be isolated and purified by conventional methods.

Where the compounds contain one or more chiral centres, then the invention includes both the resolved and unresolved forms, including diastereomers.

Pharmaceutically acceptable acid addition salts of the compounds of the formula (I) include those formed from strong acids which form non-toxic acid addition salts, such as hydrochloric, hydrobromic, sulphuric and methanesulphonic acids. Such salts are also useful for agricultural use.

The salts may be obtained by conventional procedures, e.g. by mixing solutions containing approximately equimolar amounts of the free base and desired acid, and the required salt is collected by filtration, if insoluble, or by evaporation of the solvent.

The compounds of the formula (I) and their salts are antifungal agents, useful in the curative or prophylactic treatment of fungal infections in animals, including humans. For example, they are useful in treating topical fungal infections in man caused by, among other organisms, species of *Candida, Trichophyton, Microsporum* or *Epidermophyton*, or in mucosal infections caused by *Candida albicans* (e.g. thrush and vaginal candidiasis). They can also be used in the treatment of systemic fungal infections caused by, for example, *Candida albicans, Cryptococcus neoformans, Aspergillus flavus, Aspergillus fumigatus, Coccidioides, Paracoccidioides, Histoplasma* or *Blastomyces*.

The in vitro evaluation of the antifungal activity of the compounds can be performed by determining the minimum inhibitory concentration (m.i.c.), which is the concentration of the test compounds, in a suitable medium, at which growth of the particular micro-organism fails to occur. In practice, a series of agar plates, each having the test compound incorporated at a particular concentration is inoculated with a standard culture of, for example, *Candida albicans* and each plate is then incubated for 48 hours at 37° C. The plates are then examined for the presence or absence of growth of the fungus and the appropriate m.i.c. value is noted. Other micro-organisms used in such tests can include *Aspergillus fumigatus, Trichophyton* spp, *Microsporum* spp, *Epidermophyton floccosum, Coccidioides immitis* and *Torulopsis glabrata*.

The in vivo evaluation of the compounds can be carried out at a series of dose levels by intraperitoneal or intravenous injection or by oral administration, to mice which are inoculated with, e.g., a strain of *Candida albicans* or *Aspergillus fumigatus*. Activity is based on the survival of a treated group of mice after the death of an untreated group of mice. The dose level at which the compound provides 50% protection against the lethal effect of the infection ($PD_{50}$) is noted.

For human use, the antifungal compounds of the formula (I) and their salts can be administered alone, but will generally be adminstered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the antifungal compounds of the formula (I) and their salts will be from 0.01 to 20 mg/kg (in single or divided doses) when administered by either the oral or parenteral route. Thus tablets or capsules of the compounds will contain from 5 mg to 0.5 g of active compounds for administration singly or two or more at a time as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

The compounds of the formula (I) and their salts also have activity against a variety of plant pathogenic fungi, including for example various rusts, mildews and moulds, and the compounds are thus useful for treating plants and seeds to eradicate or prevent such diseases.

The in vitro evaluation of the activity of the compounds against plant fungi can be determined by measuring their minimum inhibitory concentrations in the same way as previously described except that the plates are incubated at 30° C. for 48 hours or longer before being examined for the presence or absence of growth.

Micro-organisms used in such tests include *Cochliobolus carbonum, Pyricularia oryzae, Glomerella cingulata, Penicillium digitatum, Botrytis cinerea* and *Rhizoctonia solani*.

For agricultural and horticultural purposes the compounds and their agriculturally acceptable salts are preferably used in the form of a composition formulated as appropriate to the particular use and purpose desired. Thus the compounds may be applied in the form of dusting powders, or granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture and they are manufactured in accordance with conventional procedures. The compositions typically contain from 0.01 to 95 wt. %, preferably 0.01 to 1 wt. %, of the active ingredient. The compositions may also incorporate other active ingredients, for example, compounds having herbicidal or insecticidal activity or a further fungicide. The compounds and compositions can be applied in a number of ways, for example they can be applied directly to the plant foliage, stems, branches, seeds or roots or to the soil or other growing medium, and they may be used not only to eradicate disease, but also prophylactically to protect the plants or seeds from attack.

For field use, likely application rates of the active ingredient are from 5 to 500 g/10 ares.

The following Examples, in which all the temperatures are in °C., illustrate the invention:

EXAMPLE 1

3-(4-[4-(4-Acetamidophenyl)piperazin-1-yl]phenoxy)-2-(2,4-dichlorophenyl)-1-(1H-1,2,4-triazol-1-yl)propan-2-ol

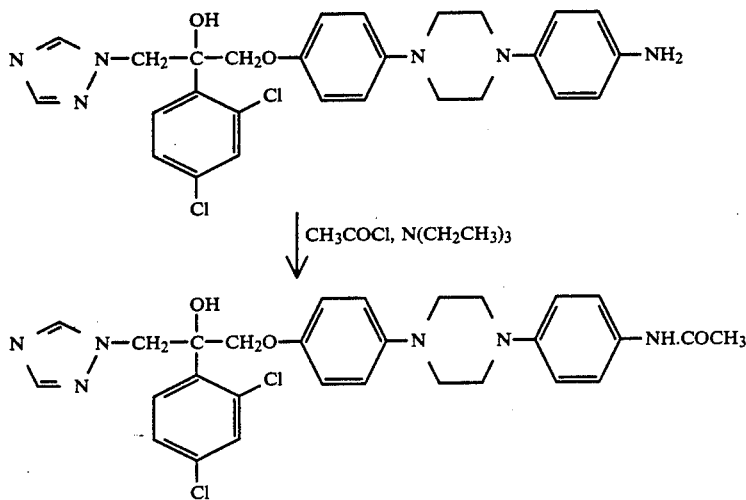

To a solution of 3-(4-[4-(4-aminophenyl)piperazin-1-yl]phenoxy)-2-(2,4-dichlorophenyl)-1-(1H-1,2,4-triazol-1-yl)propan-2-ol (see Preparation 1) (0.2 g, 0.37 mmole) and triethylamine (0.1 g, 1 mmole) in methylene chloride (20 ml) at 0° was added, dropwise, a solution of acetyl chloride (0.1 g, 1.2 mmole) in methylene chloride (1 ml). After completion of the addition the mixture was stirred at 0° for a further 1 hour and then partitioned between ethyl acetate and sodium bicarbonate solution. The separated organic phase was dried over magnesium sulphate and concentrated under reduced pressure to give a gum which on trituration with ethyl acetate yielded the desired product as a pale yellow solid, m.p. 169°-171° (0.098 g, 45%).

Analysis %: Found: C,59.7; H,5.0; N,14.1; Calculated for $C_{29}H_{30}Cl_2N_6O_3$: C,59.9; H,5.2; N,14.5.

EXAMPLE 2

3-(4-[4-(4-[2-Chloropyridin-3-carboxamido]phenyl)piperazin-1-yl]phenoxy)-2-(2,4-dichlorophenyl)-1-(1H-1,2,4-triazol-1-yl)propan-2-ol

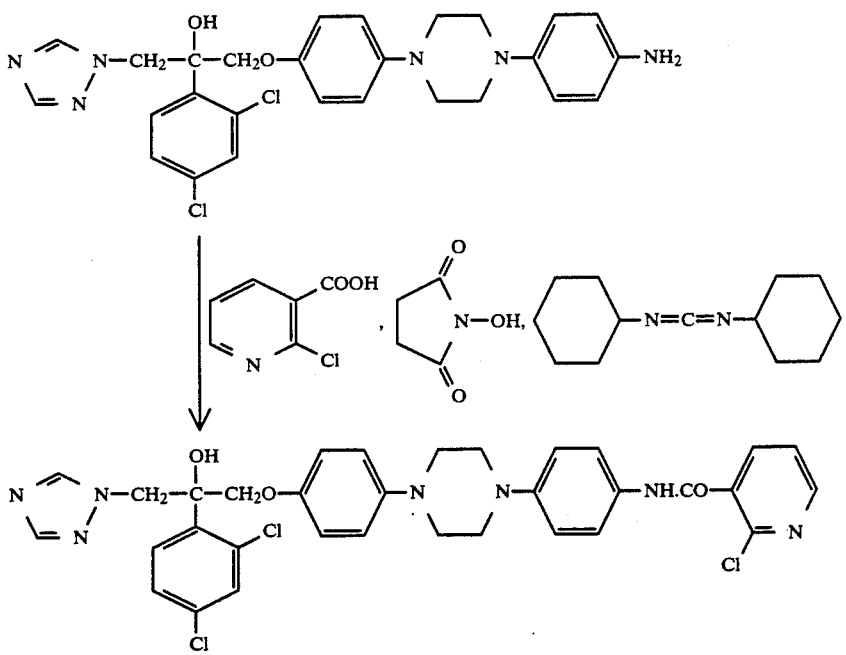

To a stirred solution of 2-chloronicotinic acid (0.087 g, 0.55 mmole) and N-hydroxysuccinimide (0.064 g, 0.55 mmole) in THF (10 ml) under nitrogen and at room temperature was added 1,3-dicyclohexylcarbodiimide (0.114 g, 0.55 mmole) and the resulting mixture was stirred for 2 hours. After this time 3-(4-[4-(4-aminophenyl)piperazin-1-yl]phenoxy)-2-(2,4-dichlorophenyl)-1-(1H-1,2,4-triazol-1-yl)propan-2-ol (see Preparation 1) (0.27 g, 0.50 mmole) was added and stirring continued for an additional 18 hours. The resulting mixture was filtered to remove insoluble material and the filtrate concentrated under reduced pressure. The residue was dissolved in ethyl acetate, washed successively with sodium bicarbonate solution then brine and dried over magnesium sulphate. After removal of the solvent under reduced pressure the residue was purified by flash chromatography on silica gel eluting with methylene chloride (90):isopropanol (10):0.88 ammonia solution (1) to yield, after collection and evaporation of appropriate fractions, the desired product, m.p. 158°-60° (0.135 g, 41%).

Analysis %: Found: C,59.0; H,4.4; N,14.1; Calculated for $C_{33}H_{30}Cl_3N_7O_3$: C,58.4; H,4.5; N,14.4.

EXAMPLE 3

2-(2,4-Dichlorophenyl)-3-(4-[4-(4-methoxycarbonylaminophenyl)-piperazin-1-yl]phenoxy)-1-(1H-1,2,4-triazol-1-yl)propan-2-ol solution and then with brine, and dried over magnesium sulphate. Concentration under reduced pressure yielded a foam which was purified by flash chromatography on silica gel eluting with ethyl acetate (90):isopropanol (10):0.88 ammonia solution (1) to yield, after collection and evaporation of appropriate fractions, the desired product as an amorphous solid, m.p. 142°-150° (0.095 g, 39%).

Analysis %: Found: C,58.6; H,5.3; N,13.8; Calculated for $C_{29}H_{30}Cl_2N_6O_4$: C,58.3; H,5.1; N,14.0.

EXAMPLE 4

3-(4-[4-(4-Allyloxycarbonylaminophenyl)piperazin-1-yl]-2-(2,4-dichlorophenyl)-1-(1H-1,2,4-triazol-1-yl)propan-2-ol

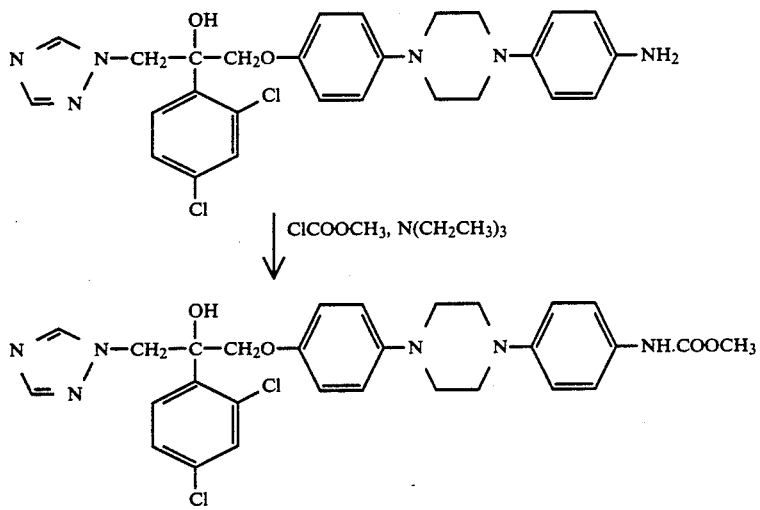

To a solution of 3-(4-[4-(4-aminophenyl)piperazin-1-yl]phenoxy)-2-(2,4-dichlorophenyl)-1-(1H-1,2,4-triazol-1-yl)propan-2-ol (see Preparation 1) (0.22 g, 0.40 mmole) and triethylamine (0.05 g, 0.49 mmole) in methylene chloride (5 ml) at 0° was added methyl chloroformate (0.043 g, 0.46 mmole) and the resulting mixture was stirred at 0° for 2 hours. After this time an additional aliquot of methyl chloroformate (0.05 g, 0.54 mmole) was added and stirring was continued at 0° for 2 hours. The resulting mixture was then diluted with methylene chloride, washed with sodium bicarbonate The title compound, m.p. 177°-9°, was prepared similarly to the procedure of Example 3 starting from the same aniline derivative and allyl chloroformate.

Analysis %: Found: C,59.9; H,5.3; N,13.3; Calculated for $C_{31}H_{32}Cl_2N_6O_4$ C,59.7; H,5.2; N,13.5.

EXAMPLE 5

2-(2,4-Dichlorophenyl)-3-(4-[4-(4-ethoxycarbonylaminophenyl)-piperazin-1-yl]phenoxy)-1-(1H-1,2,4-triazol-1-yl)propan-2-ol

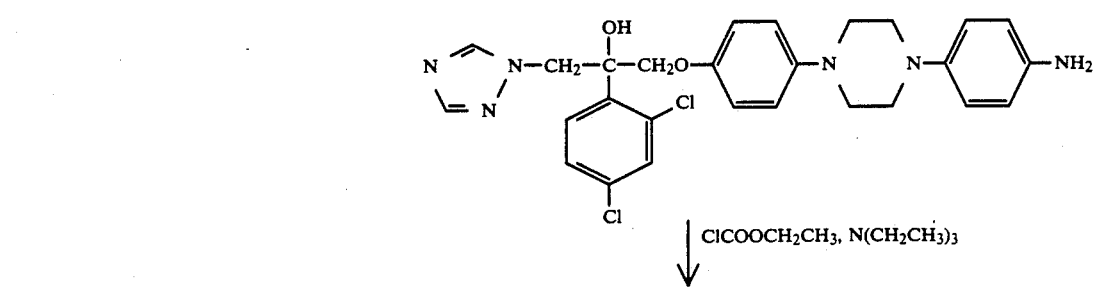

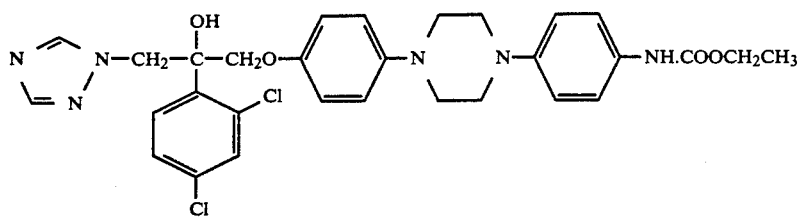

To a solution of 3-(4-[4-(4-aminophenyl)piperazin-1-yl]phenoxy)-2-(2,4-dichlorophenyl)-1-(1H-1,2,4-triazol-1-yl)propan-2-ol (see preparation 1) (0.18 g, 0.33 mmole) and triethylamine (0.1 g, 1 mmole) in methylene chloride (20 ml) at 0° was added ethyl chloroformate (0.1 g, 0.92 mmole) and the resulting mixture was stirred for 1 hour at 0°. The mixture was washed with sodium bicarbonate solution, then with brine, and dried over magnesium sulphate. Concentration under reduced pressure provided the crude product, which was purified by flash chromatography on silica gel eluting with ethyl acetate (92):isopropanol (8):0.88 ammonia solution (1) to yield, after collection and evaporation of appropriate fractions, the desired product as a pale yellow solid, m.p. 174°–176° (0.12 g, 59%).

Analysis %: Found: C,59.4; H,5.0; N,13.7; Calculated for $C_{30}H_{32}Cl_2N_6O_4$: C,58.9; H,5.3; N,13.7.

EXAMPLE 6

3-(4-[4-(4-[3-(1-Butyl)ureido]phenyl)piperazin-1-yl]phenoxy)-2-(2,4-dichlorophenyl)-1-(1H-1,2,4-triazol-1-yl)propan-2-ol A solution of 3-(4-[4-(4-aminophenyl)piperazin-1-yl]phenoxy)-2-(2,4-dichlorophenyl)-1-(1H-1,2,4-triazol-1-yl)propan-2-ol (see Preparation 1) (0.2 g, 0.37 mmole) and n-butyl isocyanate (0.1 g, 1.0 mmole) in THF (5 ml) was heated under reflux for 18 hours. The solvent was removed by concentration under reduced pressure and the product purified by flash chromatography eluting with methylene chloride (90):isopropanol (10):0.88 ammonia solution (1) to yield, after collection and evaporation of appropriate fractions, the desired product, m.p. 141°–4° (0.17 g, 72%).

Analysis %: Found: C,59.6; H,5.5; N,15.1; Calculated for $C_{32}H_{37}Cl_2N_7O_3$: C,60.2; H,5.8; N,15.3.

EXAMPLE 7

2-(2,4-Dichlorophenyl)-3-(4-[4-(4-methanesulphonamidophenyl)-piperazin-1-yl]phenoxy)-1-(1H-1,2,4-triazol-1-yl)propan-2-ol

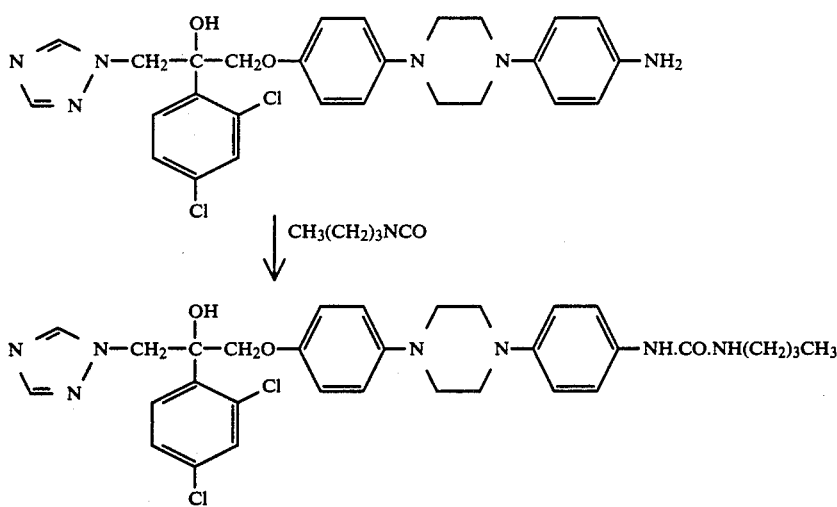

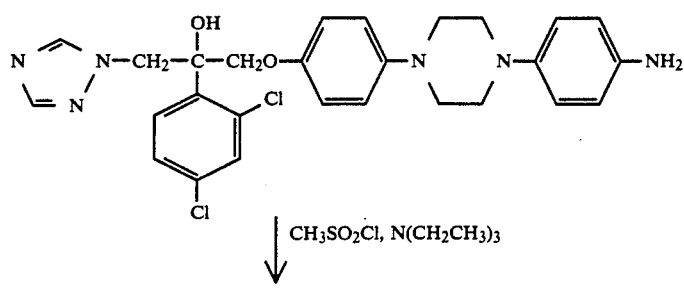

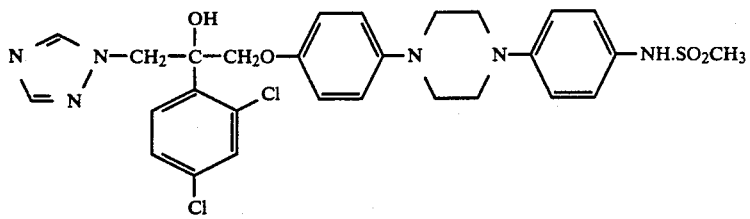

To a solution of 3-(4-[4-(4-aminophenyl)piperazin-1-yl]phenoxy)-2-(2,4-dichlorophenyl)-1-(1H-1,2,4-triazol-1-yl)propan-2-ol (see Preparation 1) (0.22 g, 0.4 mmole) and triethylamine (0.05 g, 0.49 mmole) in methylene chloride at 0° was added, dropwise, a solution of methanesulphonyl chloride (0.052 g, 0.45 mmole) in methylene chloride (1 ml), and the mixture was stirred at 0° for 2 hours. After this time an additional portion of methanesulphonyl chloride (0.05 g, 0.43 mmole) was added and stirring was continued at 0° for a further 2 hours. The reaction was then quenched by the addition of aqueous sodium bicarbonate solution and extracted with methylene chloride. The organic phase was washed with brine, dried over magnesium sulphate and concentrated under reduced pressure to provide a foam. Purification by flash chromatography on silica gel eluting with ethyl acetate (90):isopropanol (10):0.88 ammonia solution (1) yielded, after collection and evaporation of appropriate fractions, the desired product, m.p. 100°–2° (0.13 g, 58%).

Analysis %: Found: C,54.3; H,4.9; N,13.2; Calculated for $C_{28}H_{30}Cl_2N_6O_4S$: C,54.4; H,4.9; N,13.6.

EXAMPLE 8

2-(2,4-Dichlorophenyl)-3-(4-[4-(4-[(N-methyl)methanesulphonamido]piperazin-1-yl]phenoxy)-1-(1H-1,2,4-triazol-1-yl)propan-2-ol To a solution of the product of the previous Example (0.25 g, 0.4 mmole) in THF (10 ml) was added a solution of sodium hydroxide (0.018 g, 0.45 mmole) in water (1 ml) followed by dimethyl sulphate (0.062 g, 0.48 mmole), and the mixture was stirred for 1 hour at room temperature. After this time a further solution of sodium hydroxide (0.018 g, 0.45 mmole) in water (1 ml) was added, followed after 2 hours by a second portion of dimethyl sulphate (0.012 g, 0.09 mmole) and stirring was continued for 1 hour. The reaction was quenched by the addition of 2N hydrochloric acid and the mixture was allowed to stand overnight at room temperature. The resulting mixture was basified by the addition of 5N sodium hydroxide solution and extracted with methylene chloride. The combined organic extracts were washed with brine, dried over magnesium sulphate and concentrated under reduced pressure to provide a foam (0.23 g) which was purified by flash chromatography on silica gel eluting with methylene chloride (150):isopropanol (10):diethylamine (1) to yield, after collection and evaporation of appropriate fractions, the desired product, m.p. 90°–93° (0.081 g, 32%).

Analysis %: Found: C,54.8; H,5.1; N,13.0; Calculated for $C_{29}H_{32}Cl_2N_6O_4S$: C,55.1; H,5.1; N,13.3.

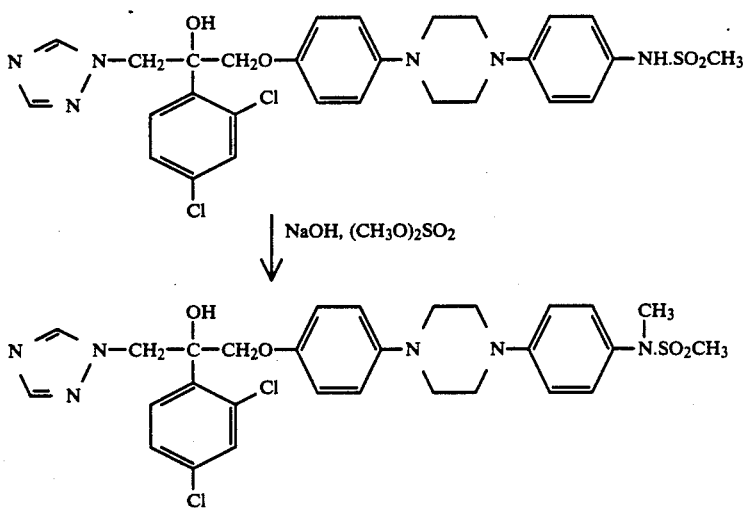

EXAMPLE 9

2-(2,4-Dichlorophenyl)-3-(4-[4-(4-ethanesulphonamidophenyl)piperazin-1-yl]phenoxy)-1-(1H-1,2,4-triazol-1-yl)propan-2-ol

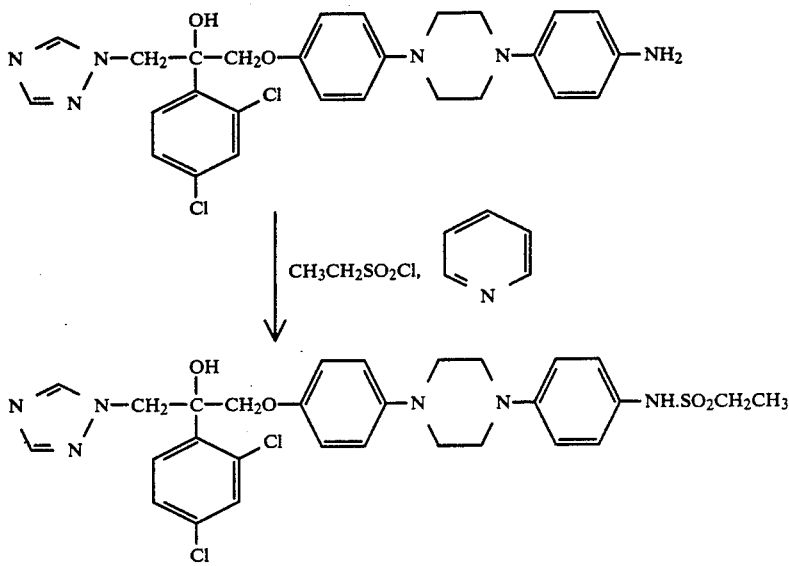

To a solution of 3-(4-[4-(4-aminophenyl)piperazin-1-yl]phenoxy)-2-(2,4-dichlorophenyl)-1-(1H-1,2,4-triazol-1yl)propan-2-ol (see Preparation 1) (0.198 g, 0.36 mmole) and pyridine (0.04 g, 0.50 mmole) in methylene chloride (15 ml) at 0° was added, dropwise, a solution of ethanesulphonyl chloride (0.054 g, 0.39 mmole) in methylene chloride (1 ml). The resulting mixture was stirred at 0° for 2 hours then for an additional 18 hours at room temperature. The mixture was then washed with aqueous citric acid then water and the organic phase was dried over magnesium sulphate. After removal of the solvent by concentration under reduced pressure, the residue was purified by flash chromatography on silica gel eluting with methylene chloride (97.5):methanol (2.5):0.88 ammonia solution (0.3) to yield, after collection and evaporation of appropriate fractions, the desired product as a foam, m.p. 88°-90° (0.136 g, 60%).

Analysis %: Found: C,52.95; H,5.01; N,12.58; Calculated for $C_{29}H_{32}Cl_2N_6O_4S.1.5\ H_2O$: C,52.88; H,5.32; N,12.77.

EXAMPLE 10

2-(2,4-Dichlorophenyl)-3-(4-[4-(4-[2-propanesulphonamido]-phenyl)piperazin-1-yl]phenoxy)-1-(1H-1,2,4-triazol-1-yl)propan-2-ol

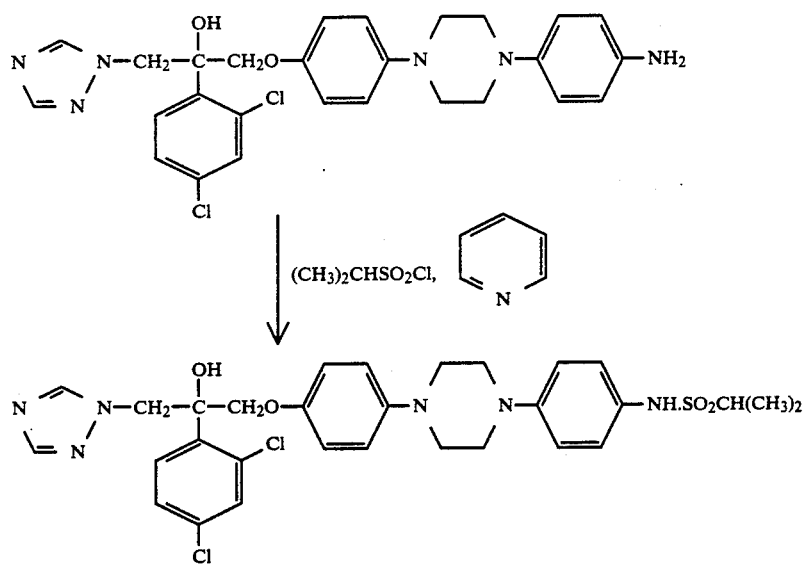

To a solution of 3-(4-[4-(4-aminophenyl)piperazin-1-yl]phenoxy)-2-(2,4-dichlorophenyl)-1-(1H-1,2,4-triazol-1-yl)propan-2-ol (see Preparation 1) (0.2 g, 0.37 mmole) and pyridine (0.06 g, 0.75 mmole) in methylene chloride (20 ml) at 0° was added 2-propanesulphonyl chloride (0.095 g, 0.66 mmole) and the reaction mixture was stirred for 2 hours at 0° followed by 24 hours at room temperature. Further portions of 2-propanesulphonyl chloride (0.05 g, 0.035 mmole) were added after this period and after an additional 24 hours. After stirring for a further 24 hours the reaction was quenched by the addition of aqueous citric acid, the organic phase separated, washed with water and dried over magnesium sulphate. After concentration under reduced pressure the black residue was purified by flash chromatography on silica gel eluting with ethyl acetate to yield, after collection and evaporation of appropriate fractions, the desired product as a foam, m.p. 74°–75° (0.172 g, 72%).

Analysis %: Found: C,55.58; H,5.49; N,12.32; Calculated for $C_{30}H_{34}Cl_2N_6O_4S \cdot 0.25\ CH_3COOC_2H_5$: C,55.77; H,5.39; N,12.59.

EXAMPLE 11

2-(2,4-Dichlorophenyl)-1-(1H-1,2,4-triazol-1-yl)-3-(4-[4-(4-[2,2,2-trifluoroethanesulphonamido]phenyl)piperazin-1-yl]phenoxy)propan-2-ol (20 ml) at 0° was added, dropwise, a solution of 2,2,2-trifluoroethanesulphonyl chloride (0.095 g, 0.52 mmole) in methylene chloride (1 ml) and the resulting mixture was stirred for 0.5 hour. The reaction was quenched by the addition of aqueous citric acid, the resulting organic phase separated, washed with water and dried over magnesium sulphate. After concentration under reduced pressure the residue was purified by flash chromatography on silica gel eluting with ethyl acetate (80):hexane (20) to yield, after collection and evaporation of appropriate fractions, the desired product as a foam, m.p. 74°–75° (0.159 g, 62%).

Analysis %: Found: C,51.10; H,4.26; N,12.19; Calculated for $C_{29}H_{29}Cl_2F_3N_6O_4S$: C,50.80; H,4.22; N,12.26.

EXAMPLE 12

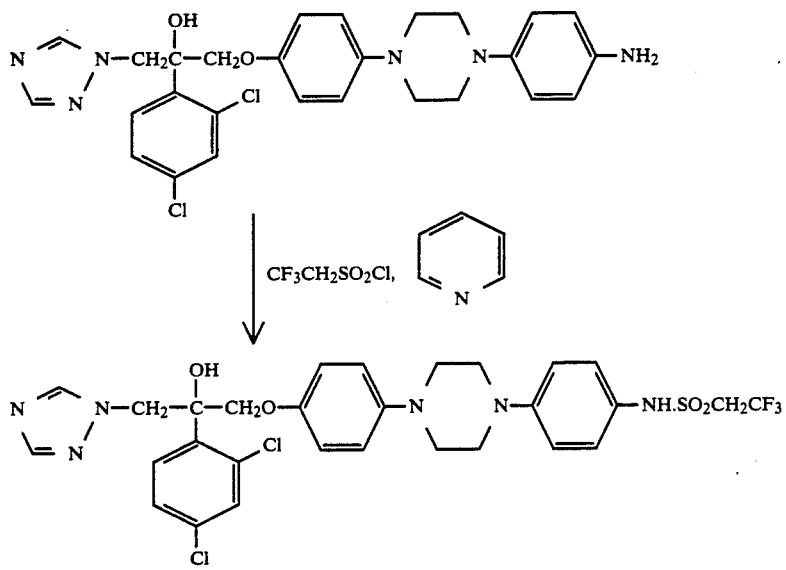

To a solution of 3-(4-[4-(4-aminophenyl)piperazin-1-yl]phenoxy)-2-(2,4-dichlorophenyl)-1-(1H-1,2,4-triazol-1-yl)propan-2-ol (see Preparation 1) (0.2 g, 0.37 mmole) and pyridine (0.06 g, 0.75 mmole) in methylene chloride 3-(4-[4-(4-[3-Chloropropanesulphonamido]phenyl)piperazin-1-yl]phenoxy)-2-(2,4-dichlorophenyl)-1-(1H-1,2,4-triazol-1-yl)propan-2-ol

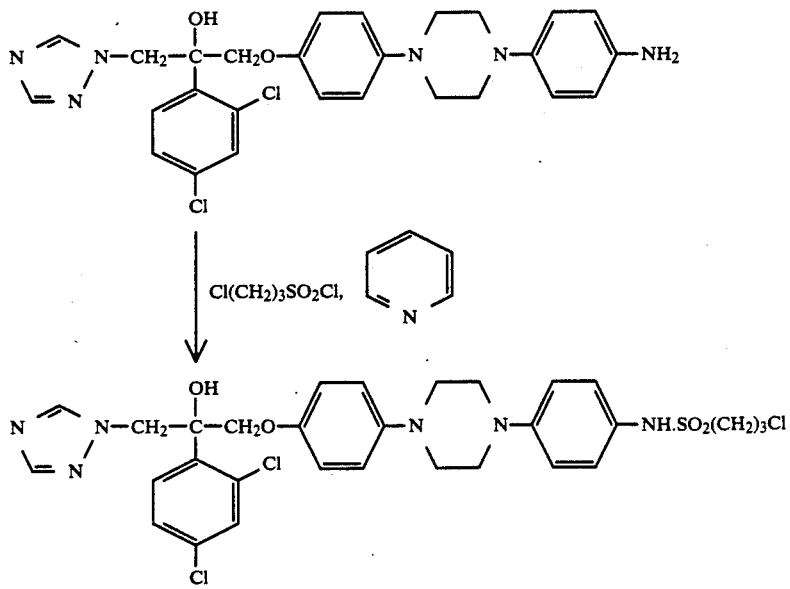

To a solution of 3-(4-[4-(4-aminophenyl)piperazin-1-yl]phenoxy)-2-(2,4-dichlorophenyl)-1-(1H-1,2,4-triazol-1-yl)propan-2-ol (see Preparation 1) (0.2 g, 0.37 mmole) and pyridine (0.1 g, 1.2 mmole) in methylene chloride (15 ml) at 0° was added, dropwise, a solution of 3-chloropropanesulphonyl chloride (0.072 g, 0.4 mmole) in methylene chloride (1 ml). The resulting mixture was stirred at 0° for 2 hours, an additional portion of 3-chloropropanesulphonyl chloride (0.036 g, 0.2 mmole) was added and stirring was continued overnight at room temperature, the reaction mixture was quenched by the addition of aqueous citric acid, the organic phase separated and washed with water. After drying over magnesium sulphate, the organic phase was concentrated under reduced pressure and the resulting gum purified by flash chromatography on silica gel eluting with ethyl acetate to yield, after collection and evaporation of appropriate fractions, the desired product as a foam, m.p. 80°–81° (0.24 g, 96%).

Analysis %: Found: C,52.87; H,4.73; N,11.97; Calculated for $C_{30}H_{33}Cl_3N_6O_4S$: C,52.98; H,4.86; N,12.36.

EXAMPLE 13

2-(2,4-Dichlorophenyl)-3-(4-[4-(4-[1,1-dioxotetrahydroisothiazolidin-2-yl]phenyl)piperazin-1-yl]phenoxy)-1-(1H-1,2,4-triazol-1-yl)propan-2-ol

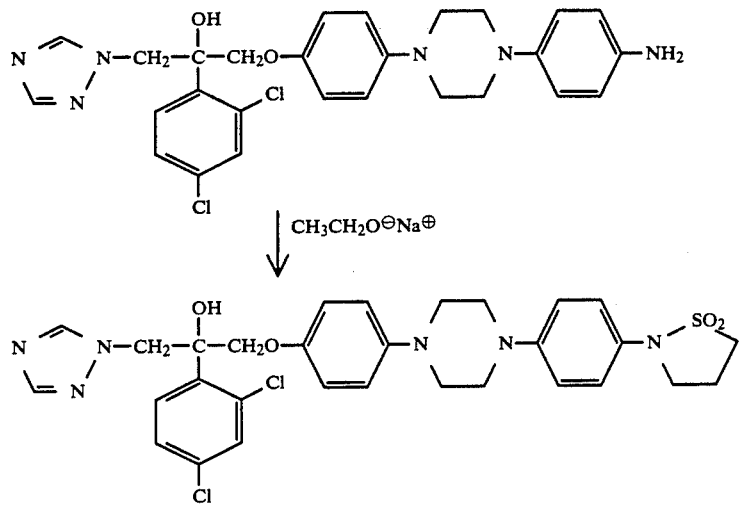

To a solution of sodium ethoxide (prepared by the addition of sodium hydride [60% dispersion in oil, 0.01 g, 0.25 mmole] to ethanol [10 ml]) was added the product of Example 12 (0.14 g, 0.2 mmole) and the resulting mixture was heated at 70° for 2 hours. The solvent was removed by concentration under reduced pressure and the residue partitioned between methylene chloride and water. After separation, the organic phase was dried over magnesium sulphate and concentrated under reduced pressure to yield a gum, which on trituration with hexane yielded the desired product, m.p. 113° (0.11 g, 81%).

Analysis %: Found: C,55.30; H,4.98; N,12.50; Calculated for $C_{30}H_{32}Cl_2N_6O_4S$: C,55.21; H,5.06; N,12.88.

EXAMPLE 14

2-(2,4-Difluorophenyl)-3-(4-[4-(4-methanesulphonamidophenyl)piperazin-1-yl]phenoxy)-1-(1H-1,2,4-triazol-1-yl)propan-2-ol

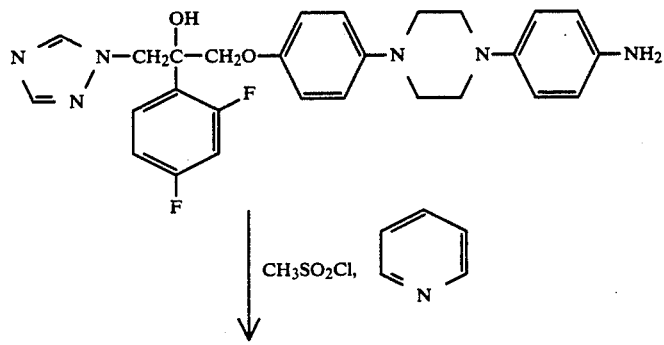

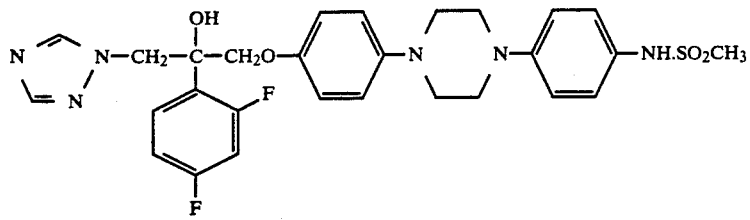

To a mixture of 3-(4-[4-(4-aminophenyl)piperazin-1-yl]phenoxy)-2-(2,4-difluorophenyl)-1-(1H-1,2,4-triazol-1-yl)propan-2-ol (see Preparation 3) (0.4 g, 0.79 mmole) and pyridine (0.08 g, 1.0 mmole) in methylene chloride (25 ml) at 0° was added a solution of methanesulphonyl chloride (0.090g, 0.79 mmole) in methylene chloride (1 ml) and the resulting mixture was stirred overnight at room temperature. After this time a second portion of methanesulphonyl chloride (0.03 g, 0.26 mmole) was added and stirring was continued for 24 hours. The reaction mixture was quenched by the addition of sodium bicarbonate solution, the organic phase separated, washed with brine and dried over magnesium sulphate. After concentration under reduced pressure, the desired product was purified by flash chromatography on silica gel eluting with ethyl acetate (98):0.88 ammonia solution (2) to yield, after collection and evaporation of appropriate fractions, the desired product, m.p. 158°-9° (0.285 g, 61%).

Analysis %: Found: C,56.80; H,5.14; N,13.98; Calculated for $C_{28}H_{30}F_2N_6O_4S \cdot 0.5H_2O$: C,57.04; H,5.9; N,14.26.

A mixture of 3-(4-[4-(4-aminophenyl)piperazin-1-yl]phenoxy)-2-(2,4-dichlorophenyl)-1-(1H-1,2,4-triazol-1-yl)propan-2-ol (see Preparation 1) (0.22 g, 0.40 mmole), triethylamine (0.05 g, 0.49 mmole) and dimethylsulphamoyl chloride (0.064 g, 0.45 mmole) in methylene chloride (5 ml) was heated under reflux for 24 hours. An additional portion of dimethylsulphamoyl chloride (0.05 g, 0.35 mmole) was then added and refluxing continued for a further 24 hours. The reaction mixture was cooled, diluted with ethyl acetate and the organic phase washed with aqueous sodium bicarbonate then brine. After drying over magnesium sulphate, the solution was concentrated under reduced pressure and purified by flash chromatography on silica gel eluting with ethyl acetate (90):isopropanol (10):diethylamine (1) to yield, after collection and evaporation of appropriate fractions, the desired product, m.p. 90°-95° (0.072 g, 28%).

Analysis %: Found: C,53.5; H,5.3; N,14.9; Calculated for $C_{29}H_{33}Cl_2N_7O_4S$: C,53.9; H,5.1; N,15.2.

EXAMPLE 15

2-(2,4-Dichlorophenyl)-3-(4-[4-(4-[(N,N-dimethylsulphamoyl)amino]phenyl)piperazin-1-yl]phenoxy)-1-(1H-1,2,4-triazol-1-yl)propan-2-ol

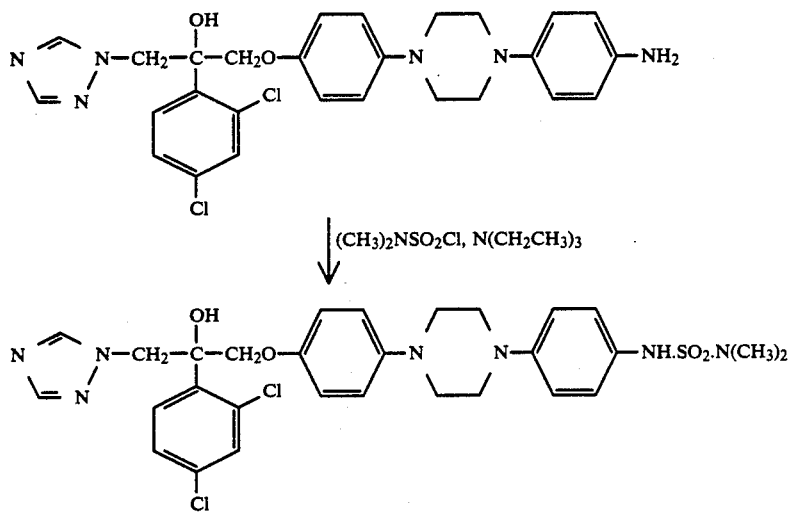

EXAMPLE 16

N-(4-[4-(4-[2-(2,4-Dichlorophenyl)-2-hydroxy-3-(1H-1,2,4-triazol-1-yl)prop-1-oxy]phenyl)piperazin-1-yl]phenyl)-N',N'-dimethylformamidine

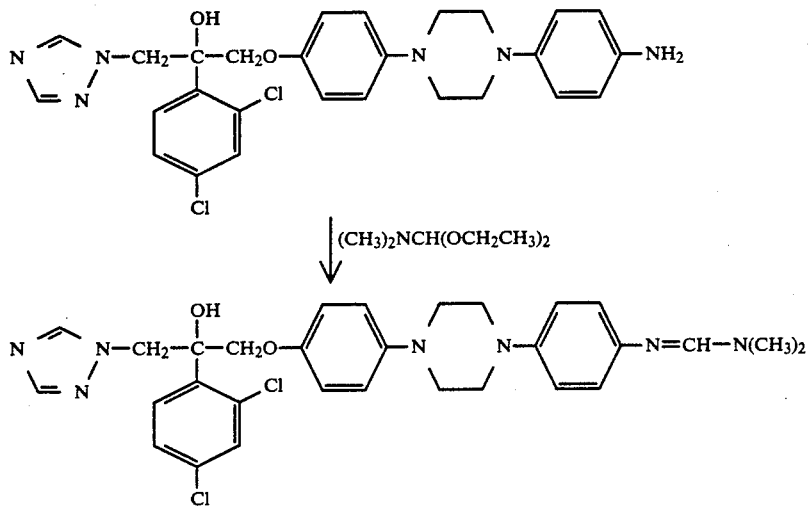

A mixture of 3-(4-[4-(4-aminophenyl)piperazin-1-yl]phenoxy)-2-(2,4-dichlorophenyl)-1-(1H-1,2,4-triazol-1-yl)propan-2-ol (see Preparation 1) (0.198 g, 0.37 mmole) and N,N-dimethylformamide diethyl acetal (0.086 g, 0.58 mmole) was heated under reflux in ethanol (10 ml) for 2.5 hours. The ethanol was removed by distillation, additional portions of N,N-dimethylformamide diethyl acetal (0.043 g, 0.29 mmole) and ethanol (5 ml) were added and distillation was continued to remove the ethanol. The resulting mixture was azeotroped with xylene (2×10 ml) under reduced pressure and the residue triturated with ether/hexane. The resulting solid was recrystallised from ethyl acetate/hexane to yield the desired product, m.p. 131°–132° (0.177 g, 79%).

Analysis %: Found: C,59.88; H,5.56; N,16.30; Calculated for $C_{30}H_{33}Cl_2N_7O_2 \cdot 0.5H_2O$: C,59.70; H,5.63; N,16.25.

EXAMPLE 17

2-(2,4-Dichlorophenyl)-3-(4-[4-(4-[1-piperazinyl]-phenyl)piperazin-1-yl]phenoxy)-1-(1H-1,2,4-triazol-1-yl)propan-2-ol

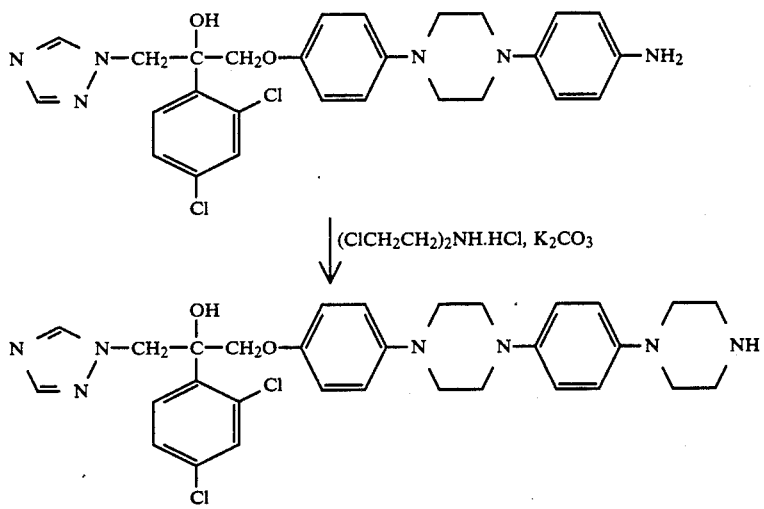

A mixture of 3-(4-[4-(4-aminophenyl)piperazin-1-yl]phenoxy)-2-(2,4-dichlorophenyl)-1-(1H-1,2,4-triazol-1-yl)propan-2-ol (see Preparation 1) (0.8 g, 1.48 mmole), bis(2-chloroethyl)amine hydrochloride (0.27 g, 1.50 mmole) and potassium carbonate (0.276 g, 2.0 mmole) in ethanol (20 ml) was heated under reflux for 190 hours. After this time the solvent was removed by concentration under reduced pressure and the residue partitioned between methylene chloride and water. The organic phase was separated, washed with water, dried over magnesium sulphate and concentrated under reduced pressure. The residual gum was purified by flash chromatography on silica gel eluting with methylene chloride (93):methanol (7):0.88 ammonia solution (1) to yield, after collection and evaporation of appropriate fractions, the desired product, m.p. 150°–151° (0.252 g, 28%).

Analysis %: Found: C,60.18; H,5.82; N,15.38; Calculated for $C_{31}H_{35}Cl_2N_7O_2 \cdot CH_3OH$: C,60.00; H,6.09; N,15.31.

EXAMPLE 18

3-(4-[4-(4-[4-Acetylpiperazin-1-yl]phenyl)piperazin-1-yl]phenoxy)-2-(2,4-dichlorophenyl)-1-(1H-1,2,4-triazol-1-yl)propan-2-ol

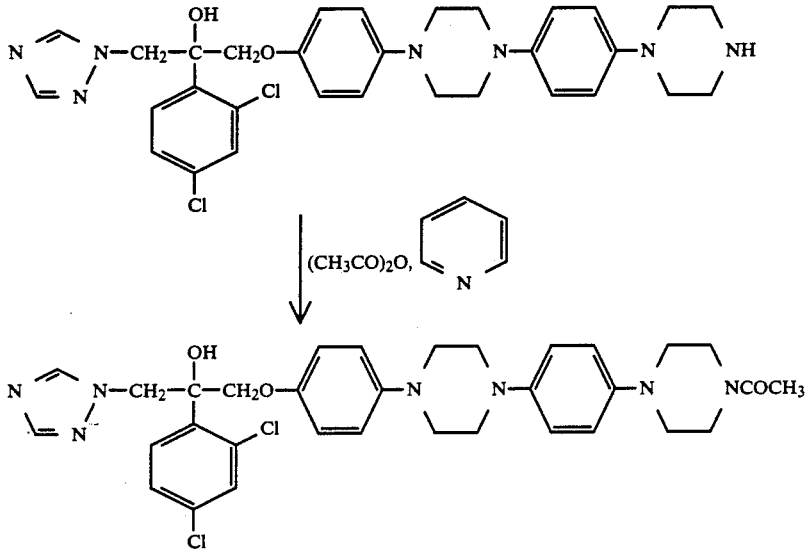

To a solution of the product of Example 17 (0.152 g, 0.25 mmole) and pyridine (0.06 g, 0.75 mmole) in methylene chloride (10 ml) was added, dropwise, acetic anhydride (0.035 g, 0.34 mmole) and the resulting mixture was stirred at room temperature for 2.5 hours. The reaction mixture was quenched by the addition of water, the organic phase separated and the aqueous layer re-extracted with methylene chloride. The combined organic extracts were washed with water, dried over magnesium sulphate and concentrated under reduced pressure. The residue was purified by flash chromatography on silica gel eluting with ethyl acetate (92):diethylamine (8) to yield, after collection and evaporation of appropriate fractions, the desired product, m.p. 130°–131° (0.119 g, 67%).

Analysis %: Found: C,58.31; H,6.40; N,13.48; Calculated for $C_{33}H_{37}Cl_2N_7O_3 \cdot 2CH_3OH$: C,58.82; H,6.30; N,13.72.

EXAMPLE 19

2-(2,4-Dichlorophenyl)-3-(4-[4-(4-[1,1-dioxotetrahydrothiazin-4-yl]phenyl)piperazin-1-yl]phenoxy)-1-(1H-1,2,4-triazol-1-yl)propan-2-ol

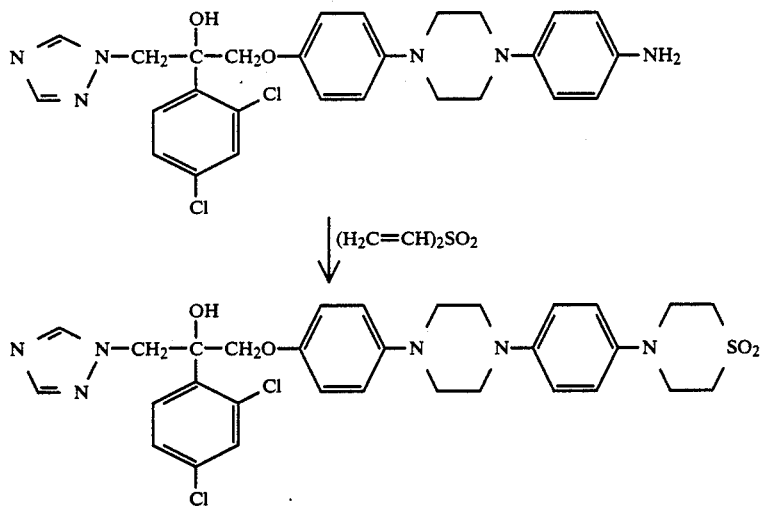

A mixture of 3-(4-[4-(4-aminophenyl)piperazin-1-yl]phenoxy)-2-(2,4-dichlorophenyl)-1-(1H-1,2,4-triazol-1-yl)propan-2-ol (see Preparation 1) (0.265 g, 0.49 mmole), divinyl sulphone (0.2 g, 1.6 mmole) and ethanol (20 ml) was heated under reflux for 7 hours. After cooling, the precipitate was removed by filtration and purified by flash chromatography on silica gel eluting with ethyl acetate to yield, after collection and evaporation of appropriate fractions, the desired product, m.p. 91°–92° (0.203 g, 59%).

Analysis %: Found: C,55.93; H,5.25; N,11.93; Calculated for $C_{31}H_{34}Cl_2N_6O_4S \cdot 0.5\ CH_3COOC_2H_5$: C,56.49; H,5.42; N,11.98.

EXAMPLE 20

1-(4-[4-(4-[2-(2,4-Dichlorophenyl)-2-hydroxy-3-(1H-1,2,4-triazol-1-yl)prop-1-oxy]phenyl)piperazin-1-yl]phenyl)pyrrolidin-2,5-dione

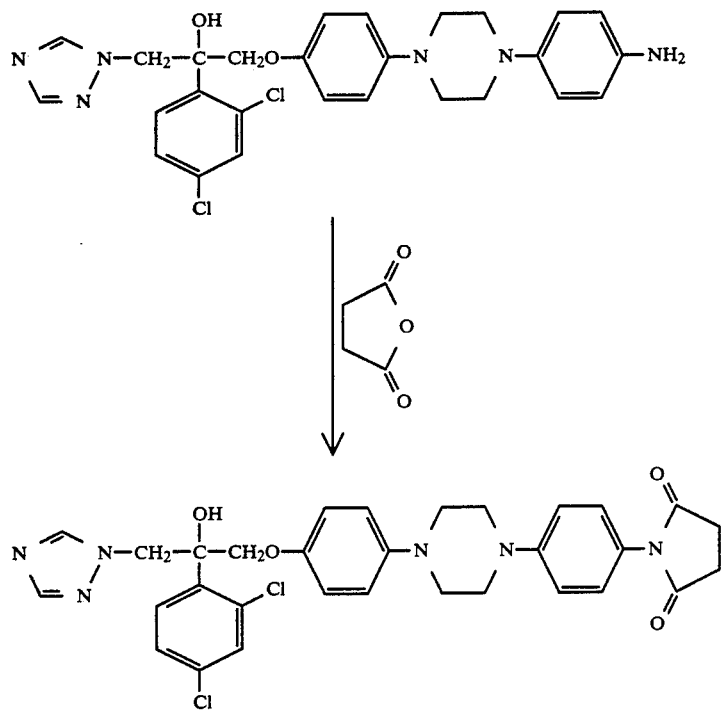

A solution of 3-(4-[4-(4-aminophenyl)piperazin-1-yl]phenoxy)-2-(2,4-dichlorophenyl)-1-(1H-1,2,4-triazol-1-yl)propan-2-ol (see Preparation 1) (0.2 g, 0.37 mmole) and succinic anhydride (0.05 g, 0.5 mmole) in acetic acid (3 ml) was heated under reflux for 4 hours. The solution was cooled, the solvent removed by concentration under reduced pressure and the resulting gum triturated with isopropanol to provide a solid (0.165 g). Purification of this solid material by flash chromatography on silica gel eluting with methylene chloride (90):isopropanol (10):acetic acid (1) yielded, after collection and evaporation of appropriate fractions, the desired product, m.p. 212°–216° (0.072 g, 31%).

Analysis %: Found: C,59.7; H,4.6; N,13.6; Calculated for $C_{31}H_{30}Cl_2N_6O_4$: C,59.9; H,4.9; N,13.5.

EXAMPLE 21

3-(4-[4-(4-[2-(2,4-Dichlorophenyl)-2-hydroxy-3-(1H-1,2,4-triazol-1-yl)prop-1-oxy]phenyl)piperazin-1-yl]phenyl)-1-methylimidazolidin-2,4-dione

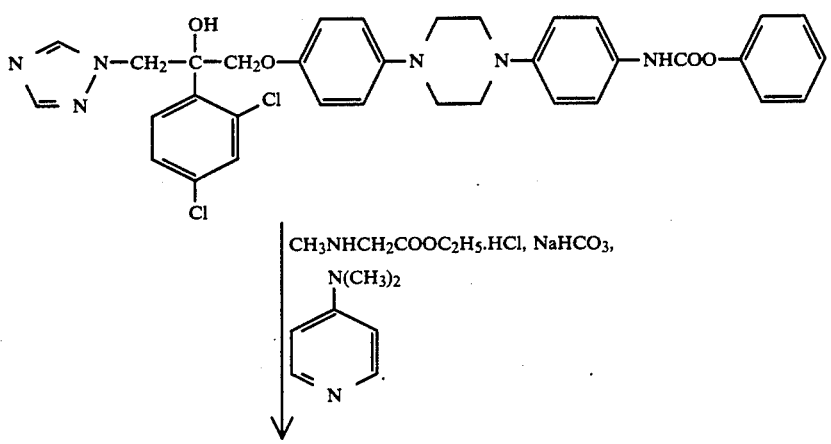

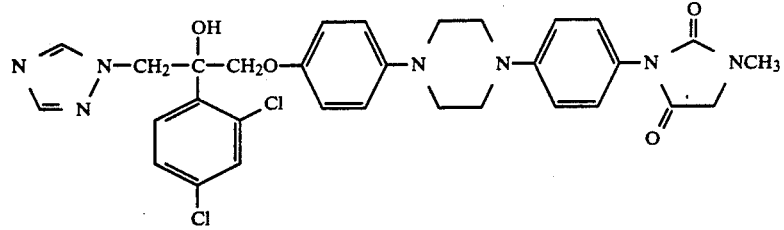

A mixture of 2-(2,4-dichlorophenyl)-3-(4-[4-(4-phenoxycarbonylaminophenyl)piperazin-1-yl]phenoxy)-1-(1H-1,2,4-triazol-1-yl)propan-2-ol (see Preparation 2) (0.3 g, 0.45 mmole), sarcosine ethyl ester hydrochloride (0.09 g, 0.58 mmole), 4-(N,N-dimethylamino)pyridine (0.03 g, 0.24 mmole) and sodium bicarbonate (0.09 g, 1 mmole) in 1,4-dioxane (30 ml) was heated under reflux for 18 hours. After cooling, the mixture was diluted with water, extracted with ethyl acetate and the organic phase washed with brine. After drying over magnesium sulphate, the organic phase was concentrated under reduced pressure to yield a gum, which on trituration with ether gave a pale yellow solid (0.260 g). Purification of this solid material by flash chromatography on silica gel eluting with methylene chloride (90):isopropanol (10):acetic acid (0.2) yielded, after collection and evaporation of appropriate fractions, the desired product as a colourless solid, m.p. 213°–215° (0.13 g, 45%).

Analysis %: Found: C,58.2; H,4.8; N,15.0; Calculated for $C_{31}H_{31}Cl_2N_7O_4$: C,58.5; H,4.9; N,15.4.

EXAMPLE 22

2-(2-Butyl)-4-(4-[4-(4-[2-(2,4-dichlorophenyl)-2-hydroxy-3-(1H-1,2,4-triazol-1-yl)prop-1-oxy]phenyl)-piperazin-1-yl]phenyl)-1,2,4-triazolin-3-one To a solution of 2-(2-butyl)-4-(4-[4-(4-hydroxyphenyl)piperazin-1-yl]phenyl)-1,2,4-triazolin-3-one (0.53 g, 1.35 mmole) in DMF (7 ml) was added sodium hydride (60% dispersion in oil, 0.042 g, 1.05 mmole - washed with dry THF to remove the oil prior to use) and the mixture was stirred under nitrogen for 1 hour. A solution of 2-(2,4-dichlorophenyl)-2-(1H-1,2,4-triazol-1-ylmethyl)oxirane (0.320 g, 1.18 mmole) in DMF (1 ml) was then added and the mixture was stirred at 70° overnight. The mixture was cooled, quenched by the addition of water and the aqueous phase was extracted with ethyl acetate. After drying over magnesium sulphate, the organic phase was concentrated under reduced pressure and the residual oil purified by flash chromatography on silica gel eluting initially with ether (497):ethanol (3):0.88 ammonia solution (1) and changing to ether (297):ethanol (3):0.88 ammonia solution (1), to yield, after collection and evaporation of appropriate fractions, the desired product as a yellow foam, m.p: 82° (0.14 g, 19%).

Analysis %: Found: C,59.63; H,5.56; N,16.62; Calculated for $C_{33}H_{36}Cl_2N_8O_3$: C,59.73; H,5.43; N,16.89.

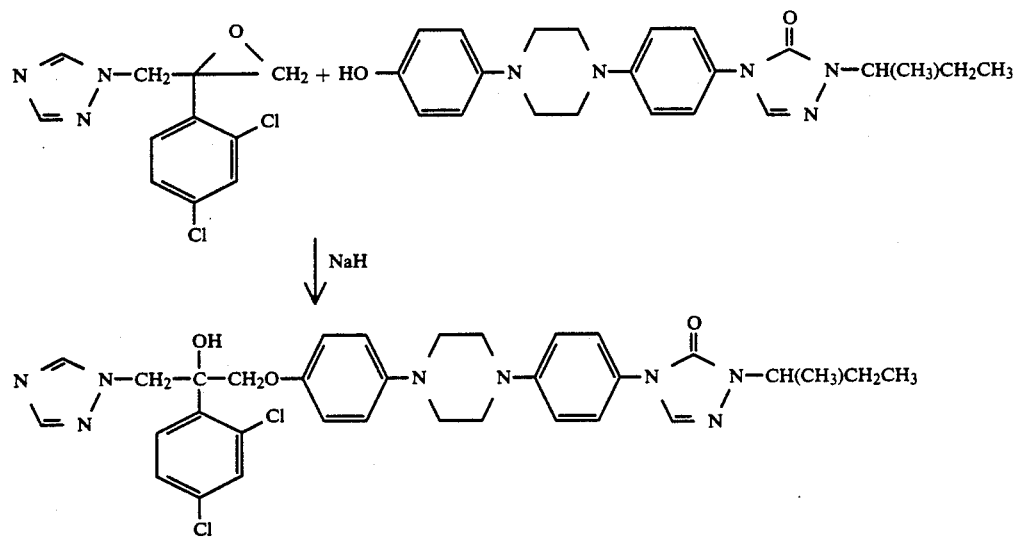

EXAMPLE 23

2-(2,4-Dichlorophenyl)-3-(4-[4-(4-pyridinyl)piperazin-1-yl]phenoxy)-1-(1H-1,2,4-triazol-1-yl)propan-2-ol

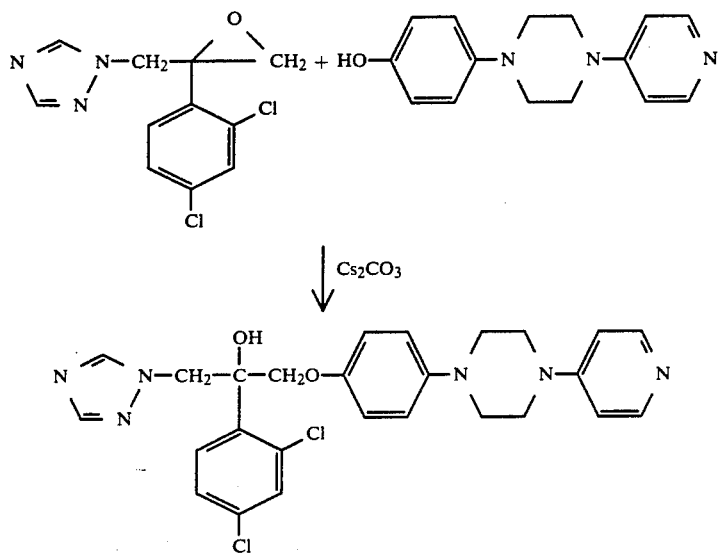

A mixture of 2-(2,4-dichlorophenyl)-2-(1H-1,2,4-triazol-1-ylmethyl)oxirane (0.3 g, 1.1 mmole), 4-(4-[4-hydroxyphenyl]piperazin-1-yl)pyridine (see Preparation 4) (0.19 g, 0.75 mmole) and cesium carbonate (0.29 g, 0.89 mmole) in DMF (18 ml) was heated at 80° under a nitrogen atmosphere for 18 hours. The DMF was removed by concentration under reduced pressure, and the residue was treated with water and extracted with methylene chloride. The organic extracts were washed with water, dried over magnesium sulphate and concentrated under reduced pressure. The residue was purified by flash chromatography on silica gel eluting with methylene chloride (94):methanol (6):0.88 ammonia solution (4) to yield, after collection and evaporation of appropriate fractions, the desired product, m.p. 98°-99° (0.25 g, 44%).

Analysis %: Found: C,58.12; H,5.07; N,15.39; Calculated for $C_{26}H_{26}Cl_2N_6O_2.0.75 H_2O$: C,57.93; H,5.11; N,15.60.

EXAMPLE 24

2-(2-Butyl)-4-(2-[4-(4-[2-(2,4-dichlorophenyl)-2-hydroxy-3-(1H-1,2,4-triazol-1-yl)prop-1-oxy]phenyl)-piperazin-1-yl]pyridin-5-yl)-1,2,4-triazolin-3-one A mixture of 2-(2,4-dichlorophenyl)-2-(1H-1,2,4-triazol-1-ylmethyl)oxirane (0.3 g, 1.1 mmole), 2-(2-butyl)-4-(2-[4-(4-hydroxyphenyl)piperazin-1-yl]pyridin-5-yl)-1,2,4-triazolin-3-one (see Preparation 5) (0.263 g, 0.67 mmole) and cesium carbonate (0.29 g, 0.89 mmole) in DMF (15 ml) was heated at 80° for 6 hours. The solvent was removed by concentration under reduced pressure and the residue was azeotroped with xylene (2×20 ml) under reduced pressure. The resulting material was partitioned between methylene chloride and water, the aqueous phase separated and re-extracted with methylene chloride. The combined organic extracts were washed with brine, dried over magnesium sulphate and concentrated under reduced pressure. The residual material was purified by flash chromatography on silica gel eluting with methylene chloride (97):methanol (3):0.88 ammonia solution (1). The product obtained, after collection and evaporation of appropriate fractions, was further purified by flash chromatography on silica gel eluting with methylene chloride (94.5):methanol (5.5):0.88 ammonia solution (4.5). The resulting material obtained, after collection and evaporation of appropriate fractions, was triturated with hexane to yield the desired product, m.p. 84°–87° (0.16 g, 36%).

Analysis %: Found: C,58.3; H,5.6; N,17.7; Calculated for $C_{32}H_{35}Cl_2N_9O_3$: C,57.8; H,5.3; N,19.0.

N.M.R. (300 MHz, CDCl₃)

δ=0.9 (t, 3H); 1.4 (d, 3H); 1.8 (m, 2H); 3.2 (m, 4H); 3.75 (m, 4H); 4.3 (q, 1H); 4.45 (m, 2H); 5.1 (m, 2H); 6.78 (d, 1H); 6.85 (d, 2H); 6.95 (d, 2H); 7.25 (d, 1H); 7.4 (s, 1H); 7.6 (s, 1H); 7.75 (d, 2H); 7.95 (s, 1H); 8.05 (s, 1H); 8.15 (s, 1H) ppm.

EXAMPLE 25

2-(2-Butyl)-4-(5-[4-(4-[2-(2,4-dichlorophenyl)-2-hydroxy-3-(1H-1,2,4-triazol-1-yl)prop-1-oxy]phenyl)-piperazin-1-yl]pyridin-2-yl)-1,2,4-triazolin-3-one The title compound, m.p. 144°–5°, was prepared similarly to the procedure of Example 24 starting from the same epoxide and 2-(2-butyl)-4-(5-[4-(4-hydroxyphenyl)piperazin-1-yl]pyridin-2-yl)-1,2,4-triazolin-3-one (see Preparation 6). In the second flash chromatography purification stage the eluent was ethyl acetate (96):methanol (4) with final trituration being unnecessary.

Analysis %: Found: C,57.94; H,5.24; N,18.70; Calculated for $C_{32}H_{35}Cl_2N_9O_3$: C,57.83; H,5.27; N,18.98.

EXAMPLE 26

2-(2-Butyl)-4-(4-[4-(4-[2-(5-chloropyridin-2-yl)-2-hydroxy-3-(1H-1,2,4-triazol-1-yl)prop-1-oxy]phenyl)-piperazin-1-yl]phenyl)-1,2,4-triazolin-3-one

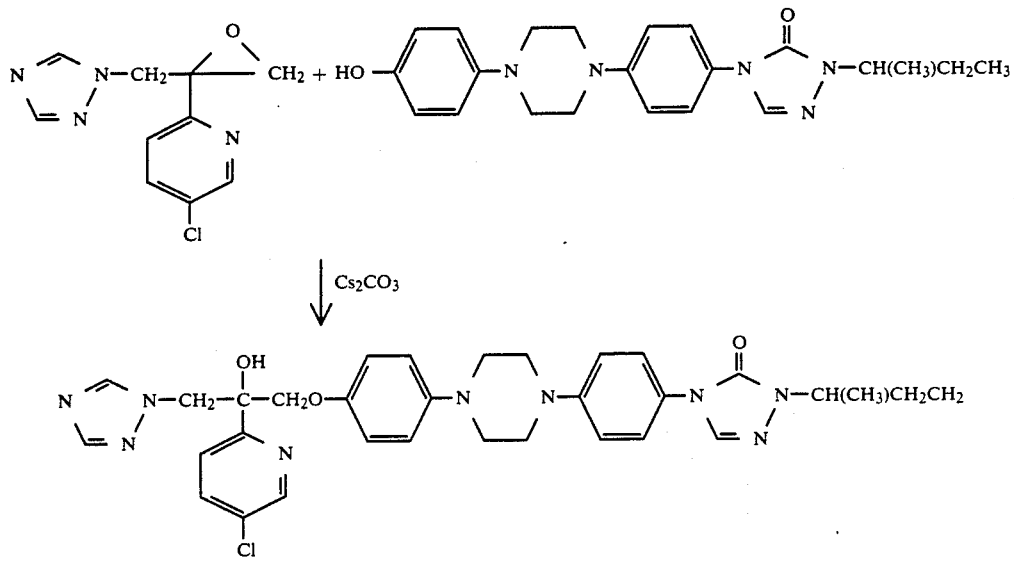

A mixture of 2-(5-chloropyridin-2-yl)-2-(1H-1,2,4-triazol-1-ylmethyl)oxirane (see EP-A-0106515) (0.115 g, 0.48 mmole), 2-(2-butyl)-4-(4-[4-(4-hydroxyphenyl)piperazin-1-yl]phenyl)-1,2,4-triazolin-3-one (0.2 g, 0.5 mmole) and cesium carbonate (0.3 g, 0.9 mmole) in DMF (10 ml) was heated at 60° for 1.5 hours. After this time an additional portion of the epoxide (0.115 g, 0.48 mmole) was added to the mixture and heating was continued at 60° overnight. After cooling, the solvent was removed by concentration under reduced pressure and the residue was partitioned between methylene chloride and water. The aqueous phase was separated, extracted with methylene chloride, the combined organic extracts washed with water and dried over magnesium sulphate. After concentration under reduced pressure, the residue was purified by flash chromatography on silica gel eluting with ethyl acetate (99):0.88 ammonia solution (1) to yield, after collection and evaporation of appropriate fractions, the desired product, m.p. 151°–152° (0.115 g, 36%).

Analysis %: Found: C,59.77; H,5.56; N,19.51; Calculated for $C_{32}H_{36}ClN_9O_3$: C,59.58; H,5.47; N,19.54.

The following Preparations, in which all temperatures are in °C., illustrate the preparation of the novel starting materials used in the previous Examples:

PREPARATION 1

3-(4-[4-(4-Aminophenyl)piperazin-1-yl]phenoxy)-2-(2,4-dichlorophenyl)-1-(1H-1,2,4-triazol-1-yl)propan-2-ol

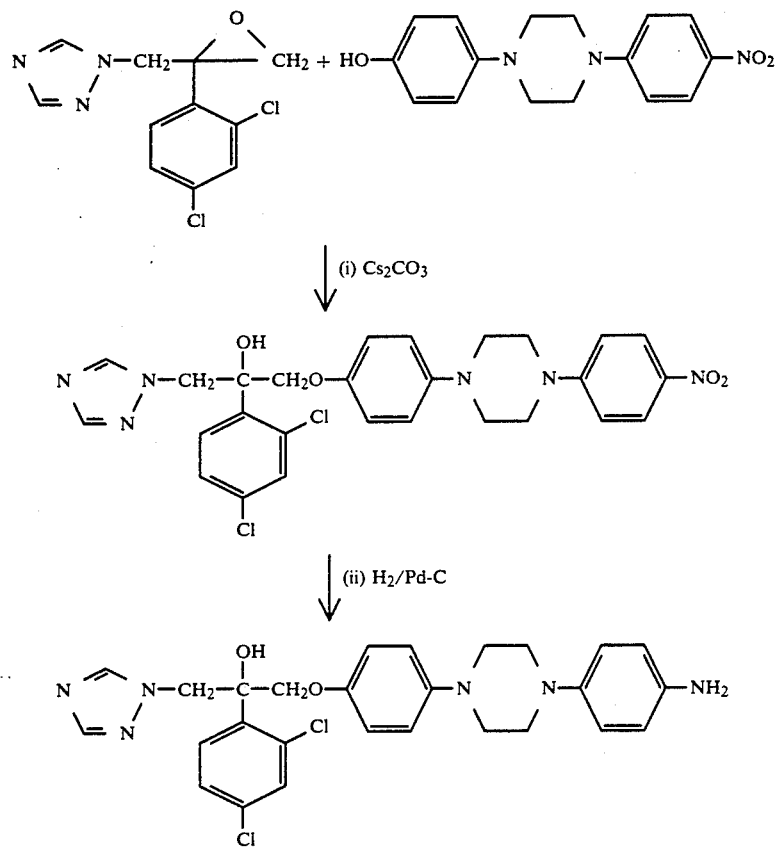

(i)
2-(2,4-Dichlorophenyl)-3-(4-[4-(4-nitrophenyl)piperazin-1-yl]phenoxy)-1-(1H-1,2,4-triazol-1-yl)propan-2-ol A stirred mixture of 2-(2,4-dichlorophenyl)-2-(1H-1,2,4-triazol-1-ylmethyl)oxirane (40 g, 0.11 mmole), 4-(4-[4-nitrophenyl]piperazin-1-yl)phenol (see EP-0228125) (35 g, 0.12 mmole) and cesium carbonate (100 g, 0.3 mmole) in DMF (500 ml) was heated at 120° for 18 hours. The mixture was cooled, diluted with methylene chloride (500 ml) and the insoluble inorganic material removed by filtration. The filtrate was concentrated under reduced pressure and the residue partitioned between methylene chloride (800 ml) and water (200 ml). The organic phase was separated, washed with water (200 ml) and dried over magnesium sulphate. After concentration under reduced pressure, the residue was purified by flash chromatography on silica gel eluting with methylene chloride (90):methanol (1):0.88 ammonia solution (0.1) to yield, after collection and evaporation of appropriate fractions, the title compounds as a viscous oil, (26.6 g, 46%), which was used directly in the next stage.

(ii)
3-(4-[4-(4-Aminophenyl)piperazin-1-yl]phenoxy)-2-(2,4-dichlorophenyl)-1-(1H-1,2,4-triazol-1-yl)propan-2-ol The product of part (i) (3.0 g, 5.2 mmole) in acetic acid (50 ml) was hydrogenated over 5% palladium on charcoal (0.3 g) at 25 p.s.i. (172 kPa) for 4 hours. The resulting mixture was filtered, the filtrate concentrated under reduced pressure and the residue partitioned between aqueous sodium carbonate and methylene chloride. The organic phase was separated and the aqueous phase further extracted with methylene chloride. The combined organic extracts were dried over magnesium sulphate and evaporated under reduced pressure to provide a foam. Trituration with petroleum ether (40°-60°) yielded the desired product, m.p. 120° (2.8 g, 98%), which was used without further purification.

PREPARATION 2

2-(2,4-Dichlorophenyl)-3-(4-[4-(4-phenoxycarbonylaminophenyl)piperazin-1-yl]phenoxy)-1-(1H-1,2,4-triazol-1-yl)propan-2-ol

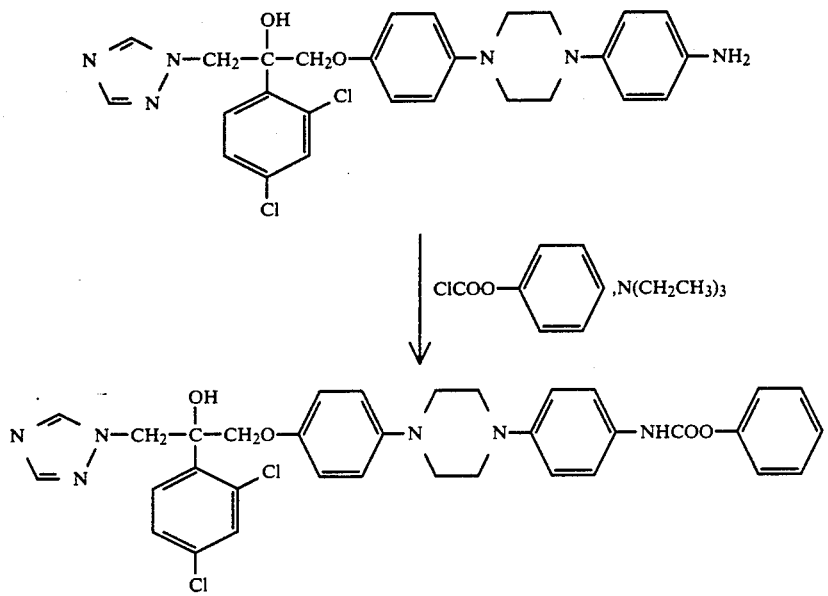

To a stirred solution of 3-(4-[4-(4-aminophenyl)piperazin-1-yl]phenoxy)-2-(2,4-dichlorophenyl)-1-(1H-1,2,4-triazol-1-yl)propan-2-ol (see Preparation 1) (0.5 g, 0.93 mmole) and triethylamine (0.16 g, 1.6 mmole) in methylene chloride (20 ml) at 0° was added, dropwise, a solution of phenyl chloroformate (0.16 g, 1.02 mmole) in methylene chloride (2 ml). After 1 hour at 0°, an additional portion of phenyl chloroformate (0.05 g, 0.32 mmole) was added and stirring continued for a further 0.5 hour. The reaction was subsequently quenched by the addition of 2N sodium hydroxide solution, methylene chloride added, the organic phase separated, washed with water, dried over magnesium sulphate and concentrated under reduced pressure to yield a foam. Trituration of this foam with ether yielded the desired product as a buff solid, (0.42 g, 68%), which was used without further purification.

PREPARATION 3

3-(4-[4-(4-Aminophenyl)piperazin-1-yl]phenoxy)-2-(2,4-difluorophenyl)-1-(1H-1,2,4-triazol-1-yl)propan-2-ol

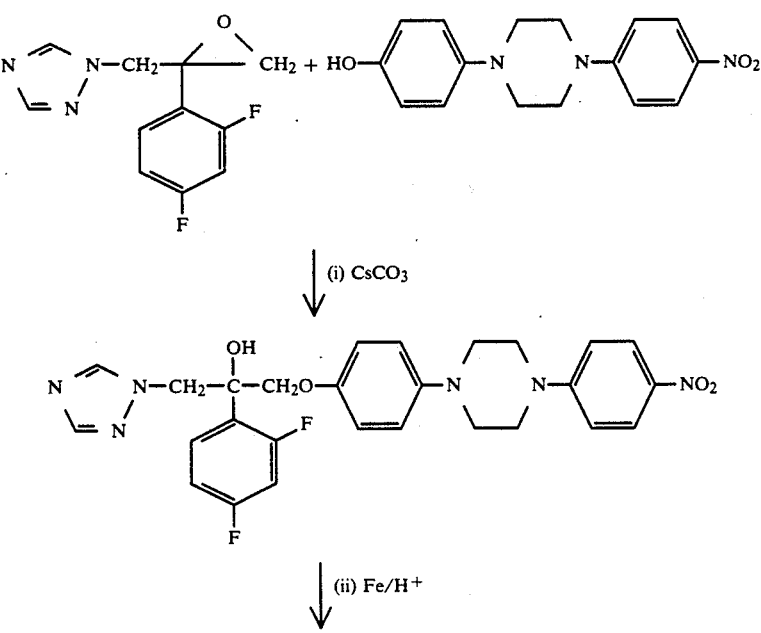

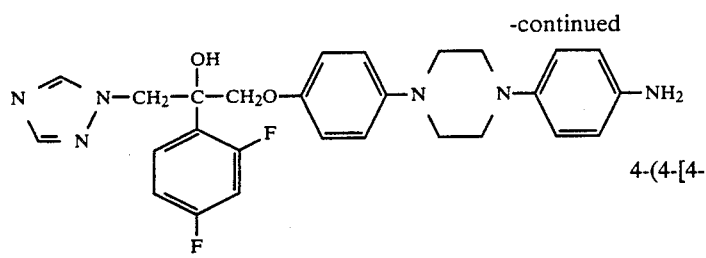

-continued

PREPARATION 4

4-(4-[4-Hydroxyphenyl]piperazin-1-yl)pyridine

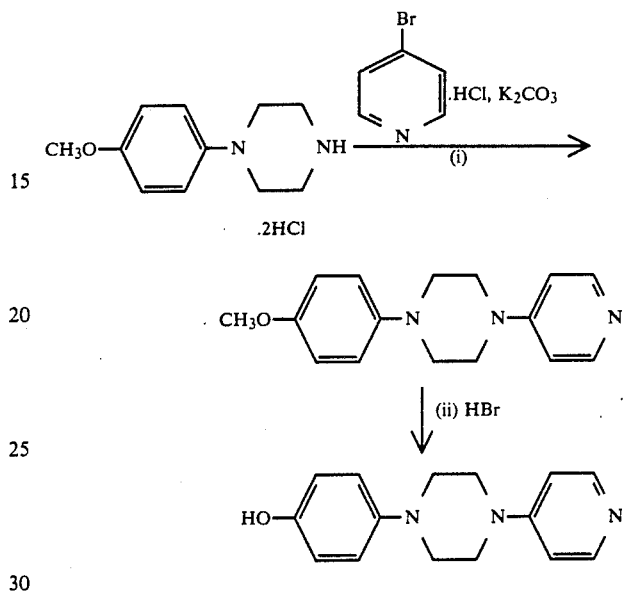

(i)
2-(2,4-Difluorophenyl)-3-(4-[4-(4-nitrophenyl)piperazin-1-yl]phenoxy)-1-(1H-1,2,4-triazol-1-yl)propan-2-ol A mixture of 2-(2,4-difluorophenyl)-2-(1H-1,2,4-triazol-1-ylmethyl)oxirane (3.3 g, 13.9 mmole), 4-(4-[4-nitrophenyl]piperazin-1-yl)phenol (3.0 g, 10 mmole) and cesium carbonate (4.8 g, 14.7 mmole) in DMF (20 ml) was heated at 80° overnight. After cooling, the solvent was removed by concentration under reduced pressure and the residue was partitioned between ethyl acetate and water. The organic phase was separated, washed with brine and dried over magnesium sulphate. The solution was concentrated under reduced pressure and purified by flash chromatography on silica gel eluting with ethyl acetate (10):hexane (1) to yield, after collection and evaporation of appropriate fractions, the desired product, m.p. 187°-189° (0.9 g, 17%).

Analysis %: Found: C,59.77; H,4.80; N,15.11; Calculated for $C_{27}H_{26}F_2N_6O_4.0.25\ CH_3COOC_2H_5$: C,60.16; H,5.01; N,15.04.

(ii)
3-(4-[4-(4-Aminophenyl)piperazin-1-yl]phenoxy)-2-(2,4-difluorophenyl)-1-(1H-1,2,4-triazol-1-yl)propan-2-ol A mixture of the product of part (i) (0.98 g, 1.8 mmole) and iron powder (0.31 g, 5.5 mmole) in 50% aqueous ethanol (60 ml) was heated to 90° and then a solution of concentrated hydrochloric acid (0.025 ml) in ethanol (0.5 ml) was cautiously added. Heating was continued for 0.75 hour, the mixture neutralised by the addition of solid sodium bicarbonate and the hot solution filtered to remove insoluble material. The filtrate was concentrated under reduced pressure and the residue purified by flash chromatography on silica gel eluting with methylene chloride (20):methanol (1):0.88 ammonia solution (0.2) to yield, after collection and evaporation of appropriate fractions, the desired product, m.p. 199°-200° (0.54 g, 59%).

Analysis %: Found: C,63.52; H,5.75; N,16.29; Calculated for $C_{27}H_{28}F_2N_6O_2.0.125\ CH_3COOC_2H_5$: C,63.76; H,5.60; N,16.23.

(i) 4-(4-[4-Methoxyphenyl]piperazin-1-yl)pyridine

A mixture of 1-(4-methoxyphenyl)piperazine dihydrochloride (2.64 g, 10 mmole), 4-bromopyridine hydrochloride (4 g, 20 mmole) and potassium carbonate (4.2 g, 30 mmole) in DMF (30 ml) was heated at 90° for 72 hours. The resulting mixture was cooled, partitioned between water and toluene, the aqueous phase separated and re-extracted with toluene. The combined organic extracts were washed with water, dried over magnesium sulphate and concentrated under reduced pressure to yield, after trituration with ether, a solid (0.9 g). This solid was purified by flash chromatography on silica gel eluting with methylene chloride (95):methanol (5):0.88 ammonia solution (4) to yield, after collection and evaporation of appropriate fractions and recrystallisation from ethyl acetate, the desired product, m.p. 183°-184° (0.77 g, 28%).

Analysis %: Found: C,70.80; H,7.09; N,15.29; Calculated for $C_{16}H_{19}N_3O$: C,71.38; H,7.06; N,15.61.

(ii) 4-(4-[4-Hydroxyphenyl]piperazin-1-yl)pyridine

A mixture of the product of part (i) (0.7 g, 2.6 mmole) and 48% hydrobromic acid (10 ml) was heated under reflux under a nitrogen atmosphere overnight. The hydrobromic acid was removed by concentration under reduced pressure, the residue dissolved in water and the solution obtained was basified with aqueous sodium bicarbonate solution. The resulting precipitate was removed by filtration and washed with methylene chloride to yield the desired product, m.p. 275°-276° (0.276 g, 41%).

Analysis %: Found: C,69.50; H,6.75; N,16.48; Calculated for $C_{15}H_{17}N_3O.0.25\ H_2O$: C,69.36; H,6.74; N,16.19.

PREPARATION 5

2-(2-Butyl)-4-(2-[4-(4-hydroxyphenyl)piperazin-1-yl]pyridin-5-yl)-1,2,4-triazolin-3-one

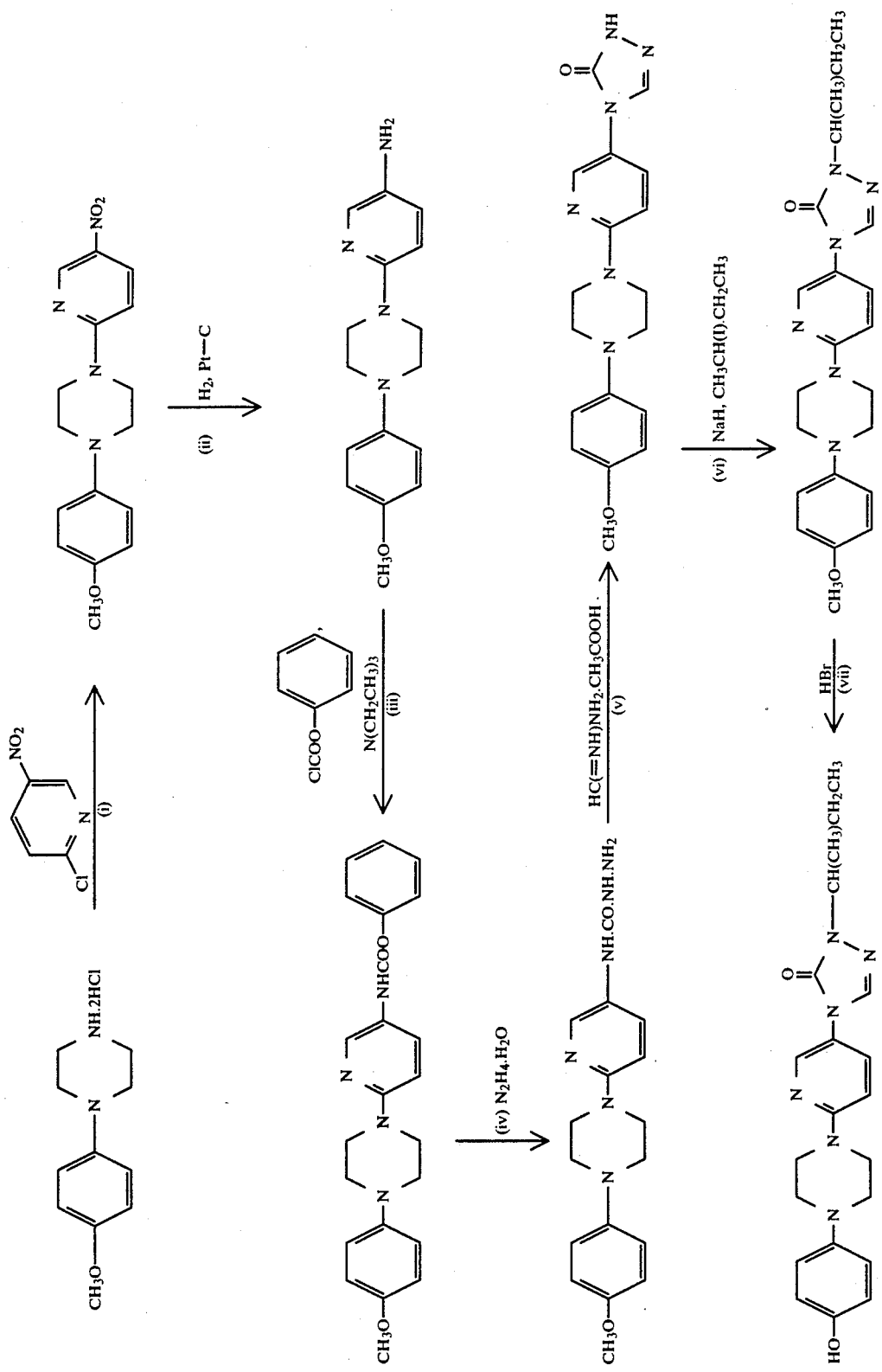

(i)
2-(4-[4-Methoxyphenyl]piperazin-1-yl)-5-nitropyridine

A mixture of 1-(4-methoxyphenyl)piperazine dihydrochloride (5.30 g, 20 mmole), 2-chloro-5-nitropyridine (3.2 g, 20 mmole) and potassium carbonate (4.14 g, 30 mmole) in DMF (20 ml) was heated at 120° for 66 hours. The reaction mixture was cooled, diluted with water and the resulting precipitate collected by filtration. To this solid was added methanol (200 ml) and the mixture was heated under reflux for 0.17 hour. After cooling, the solid was collected by filtration and dried to yield the desired product, m.p. 165°–6° (4.0 g, 64%), which was used without further purification.

(ii)
5-Amino-2-(4-[4-methoxyphenyl]piperazin-1-yl)pyridine

A suspension of the product of part (i) (4.0 g, 12 mmole) in ethanol (150 ml) was hydrogenated at 45 p.s.i. (310 kPa) over 5% platinum on carbon (0.1 g) for 5 hours. After this time an additional portion of the catalyst (0.1 g) was added and hydrogenation was continued at room temperature for a further 48 hours. The catalyst was removed by filtration and the filtrate concentrated under reduced pressure. The dark residue was purified by flash chromatography on silica gel eluting with ethyl acetate (97):methanol (3) to yield, after collection and evaporation of appropriate fractions, the desired product, m.p. 134°–135° (1.2 g, 33%), which was used without further purification.

(iii)
2-(4-[Methoxyphenyl]piperazin-1-yl)-5-phenoxycarbonylaminopyridine

To a mixture of the product of part (ii) (1.2 g, 4.2 mmole) and triethylamine (0.5 g, 5 mmole) in methylene chloride (20 ml) was added, dropwise, phenyl chloroformate (0.8 g, 5.1 mmole) and the resulting mixture was stirred at room temperature for 20 hours. The reaction was quenched by the addition of water, the aqueous phase separated and re-extracted with methylene chloride. The combined organic extracts were washed with aqueous sodium bicarbonate solution then water, dried over magnesium sulphate and concentrated under reduced pressure to provide a solid. Trituration of this solid material with ethanol yielded the desired product, m.p. 197°–198° (1.4 g, 83%), which was used without further purification.

(iv)
4-(2-[4-(4-Methoxyphenyl)piperazin-1-yl]pyridin-5-yl)semicarbazide

A mixture of the product of part (iii) (2.8 g, 6.9 mmole) and hydrazine hydrate (7.5 ml, 150 mmole) in 1,4-dioxane (50 ml) was heated under reflux for 1.5 hours. The cooled mixture was filtered to provide a solid which was washed with ether to yield the desired product, m.p. 280°–282° (2.0 g, 85%), which was used without further purification.

(v)
4-(2-[4-(4-Methoxyphenyl)piperazin-1-yl]pyridin-5-yl)-1,2,4-triazolin-3(2H)-one A mixture of the product of part (iv) (2.0 g, 5.8 mmole) and formamidine acetate (1.0 g, 10 mmole) in dimethyl sulphoxide (25 ml) was heated at 100° for 2 hours. After cooling, the mixture was poured into water (250 ml) and the resulting precipitate was collected by filtration and dried in vacuo to yield the desired product, m.p. 260°–261° (1.7 g, 83%), which was used without further purification.

(vi)
2-(2-Butyl)-4-(2-[4-(4-methoxyphenyl)piperazin-1-yl]pyridin-5-yl)-1,2,4-triazolin-3-one To a solution of the product of part (v) (1.7 g, 4.8 mmole) in dimethyl sulphoxide (25 ml) (heating required to facilitate dissolution) was added, cautiously, sodium hydride (60% dispersion in oil, 0.40 g, 10 mmole) and the mixture was stirred at room temperature for 0.3 hour. After this time, 2-iodobutane (3.6 g, 20 mmole) was added, dropwise, and the mixture was heated at 60°–70° for 1.2 hours. The resulting dark solution was poured into water and the solid removed by filtration. Purification of this material by flash chromatography on silica gel eluting with ethyl acetate (90):hexane (10) yielded, after collection and evaporation of appropriate fractions, a semi-solid. Trituration of this material with ether yielded the desired product as a solid, m.p. 172°–173° (0.55 g, 28%), which was used without further purification.

(vii)
2-(2-Butyl)-4-(2-[4-(4-hydroxyphenyl)piperazin-1-yl]pyridin-5-yl)-1,2,4-triazolin-3-one A mixture of the product of part (vi) (0.48 g, 1.17 mmole) and 48% hydrobromic acid was heated under reflux for 6.5 hours. After this time the hydrobromic acid was removed by concentration under reduced pressure and the residue basified by the addition of aqueous sodium bicarbonate solution. The resulting mixture was extracted with methylene chloride, the organic extracts washed with water, dried over magnesium sulphate and concentrated under reduced pressure. The residue was purified by flash chromatography on silica gel eluting with methylene chloride (95):methanol (5):0.88 ammonia solution (0.8) to yield, after collection and evaporation of appropriate fractions, the desired product, m.p. 195°–196° (0.287 g, 62%), which was used without further purification.

PREPARATION 6
2-(2-Butyl)-4-(5-[4-(4-hydroxyphenyl)piperazin-1-yl]pyridin-2-yl)-1,2,4-triazolin-3-one

(i)
5-(4-[4-Methoxyphenyl]piperazin-1-yl)-2-nitropyridine

The title compound, m.p. 186°–8°, was prepared similarly to the procedure of Preparation 5(i) starting from the same piperazine and 5-bromo-2-nitropyridine. The product obtained was used without further purification.

(ii)
2-Amino-5-(4-[4-methoxyphenyl]piperazin-1-yl)pyridine

A suspension of the product of part (i) (0.65 g, 2.0 mmole) in ethyl acetate (30 ml) was hydrogenated over 5% platinum on carbon (25 mg) at 45 p.s.i. (310 kPa) and at 50° for 12 hours, followed by 45 hours at room temperature. The resulting mixture was filtered to remove the catalyst, concentrated under reduced pressure and the residue triturated with ether to yield the desired product, m.p. 182°–188° (0.28 g, 50%), which was used without further purification.

(iii)
5-(4-[4-Methoxyphenyl]piperazin-1-yl)-2-phenoxycarbonylaminopyridine

The title compound, m.p. 130°-2°, was prepared similarly to the procedure of Preparation 5(iii) starting from the product of part (ii). The crude material obtained was purified by flash chromatography on silica gel eluting with ethyl acetate (60):hexane (40). The product obtained after collection and evaporation of appropriate fractions, was used without further purification.

(iv)
4-(5-[4-(4-Methoxyphenyl)piperazin-1-yl]pyridin-2-yl)semicarbazide

The title compound, m.p. 260°-3°, was prepared similarly to the procedure of Preparation 5(iv) starting from the product of part (iii). The product obtained was used without further purification.

(v)
4-(5-[4-(4-Methoxyphenyl)piperazin-1-yl]pyridin-2-yl)-1,2,4-triazolin-3(2H)-one The title compound, m.p. 268°-71°, was prepared similarly to the procedure of Preparation 5(v) starting from the product of part (iv). The product obtained was used without further purification.

(vi)
2-(2-Butyl)-4-(5-[4-(4-methoxyphenyl)piperazin-1-yl]pyridin-2-yl)-1,2,4-triazolin-3-one The title compound, m.p. 139°-140°, was prepared similarly to the procedure of Preparation 5(vi) starting from the product of part (v). The eluent used in the flash chromatography stage was ethyl acetate (1):hexane (1). The product obtained was used without further purification.

(vii)
2-(2-Butyl)-4-(5-[4-(4-hydroxyphenyl)piperazin-1-yl]pyridin-2-yl)-1,2,4-triazolin-3-one The title compound, m.p. 144°-5°, was prepared similarly to the procedure of Preparation 5(vii) starting from the product of part (vi). Flash chromatography was unnecessary and the product obtained was used without further purification.

We claim:
1. A compound of the formula

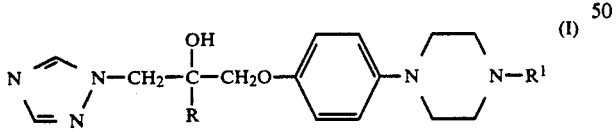

(I)

or a pharmaceutically acceptable acid addition salt thereof wherein R is 5-chloropyridin-2-yl, phenyl, difluorophenyl or dichlorophenyl and $R^1$ is para-substituted phenyl wherein said substituent is (1) —NHCOR² where $R^2$ is alkyl having one to four carbon atoms, cycloalkyl having three to seven carbon atoms, 2-chloropyridin-3-yl, alkoxy having one to four carbon atoms, allyloxy or alkylamino having one to four carbon atoms, (2) —N(R⁴)SO₂R³ where $R^3$ is alkyl having one to four carbon atoms, haloalkyl having one to four carbon atoms or dialkylamino each alkyl having one to four carbon atoms, $R^4$ is hydrogen or methyl; or $R^3$ and $R^4$ together form an alkylene group having three or four carbon atoms, (3) —N=CH—N(R⁶)₂ where $R^6$ is alkyl having one to four carbon atoms,

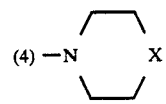

where
X is O, SO₂ or N-R⁵ where $R^5$ is hydrogen, alkyl having one to four carbon atoms or alkanoyl having one to four carbon atoms or

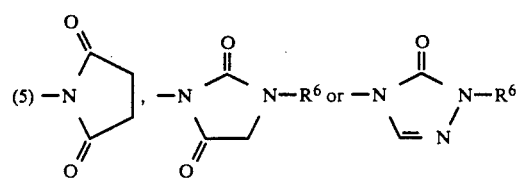

where $R^6$ is alkyl having one to four carbon atoms; or pyridinyl group optionally substituted with a group of the formula

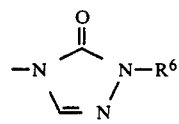

where $R^6$ is alkyl having one to four carbon atoms.

2. A compound of claim 1, wherein R is dichlorophenyl and $R^1$ is para-substituted phenyl.

3. The compound of claim 2, wherein R is 2,4-dichlorophenyl and $R^1$ is

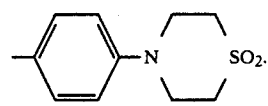

4. The compound of claim 2, wherein R is 2,4-dichlorophenyl and $R^1$ is

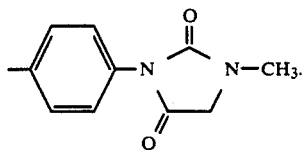

5. A compound of claim 1, wherein R is difluorophenyl and $R^1$ is para-substituted phenyl.

6. The compound of claim 5, wherein R is 2,4-difluorophenyl and $R^1$ is

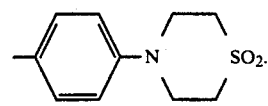

7. The compound of claim 5, wherein R is 2,4-difluorophenyl and $R^1$ is

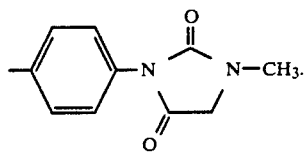

8. A pharmaceutical antifungal composition for use in humans comprising an antifungal effective amount of a compound of claim 1.

9. An agricultural composition for fungicidal use comprising an antifungal effective amount of a compound of claim 1, together with an agriculturally acceptable diluent or carrier.

10. A method of treating a plant or seed to cure or prevent a fungal infection, which comprises administering to said plant or seed, or to the locus of said plant or seed, an antifungal effective amount of a compound of claim 1.

* * * * *